US012734375B2

(12) United States Patent
Stokes et al.

(10) Patent No.: US 12,734,375 B2
(45) Date of Patent: Sep. 15, 2026

(54) SHIELDING FEATURES FOR ULTRASONIC BLADE OF A SURGICAL INSTRUMENT

(71) Applicant: Cilag GmbH International, Zug (CH)

(72) Inventors: Michael J. Stokes, Cincinnati, OH (US); Jacob S. Gee, Cincinnati, OH (US); Kevin D. Felder, Cincinnati, OH (US); Tylor C. Muhlenkamp, Cincinnati, OH (US); Patrick J. Scoggins, Loveland, OH (US); Craig N. Faller, Batavia, OH (US); Jeffrey D. Messerly, Cincinnati, OH (US); David J. Cagle, Cincinnati, OH (US); William B. Weisenburgh, II, Maineville, OH (US)

(73) Assignee: Cilag GmbH International, Zug (CH)

( * ) Notice: Subject to any disclaimer, the term of this patent is extended or adjusted under 35 U.S.C. 154(b) by 39 days.

(21) Appl. No.: 18/470,765

(22) Filed: Sep. 20, 2023

(65) Prior Publication Data

US 2024/0009488 A1 Jan. 11, 2024

Related U.S. Application Data

(63) Continuation of application No. 16/890,198, filed on Jun. 2, 2020, now Pat. No. 11,801,399, which is a (Continued)

(51) Int. Cl.
*A61B 17/32* (2006.01)
*A61N 7/00* (2006.01)
(Continued)

(52) U.S. Cl.
CPC ........ *A61N 7/00* (2013.01); *A61B 17/320068* (2013.01); *A61B 17/320092* (2013.01);
(Continued)

(58) Field of Classification Search
CPC .... A61B 17/320092; A61B 17/320068; A61B 2018/0063; A61B 2018/00011;
(Continued)

(56) References Cited

U.S. PATENT DOCUMENTS 5,322,055 A 6/1994 Davison et al.
5,873,873 A 2/1999 Smith et al.
(Continued)

FOREIGN PATENT DOCUMENTS

CN 1901847 A 1/2007
CN 101674780 A 3/2010
(Continued)

OTHER PUBLICATIONS

Chinese Office Action, Notification of First Office Action, dated Jan. 23, 2018 for Application No. CN 201480073943.5, 2 pgs.
(Continued)

*Primary Examiner* — Anh T Dang
(74) *Attorney, Agent, or Firm* — FBT Gibbons LLP

(57) ABSTRACT

An apparatus comprises a body, a shaft assembly, an end effector, and a shield member. The shaft assembly extends distally from the body. The end effector is located at a distal end of the shaft assembly. The end effector comprises an ultrasonic blade and a clamp arm. The ultrasonic blade is configured to vibrate at an ultrasonic frequency. The clamp arm is movable toward the ultrasonic blade to compress tissue against the ultrasonic blade. The shield member is selectively movable from a first position to a second position in response to movement of the clamp arm toward the ultrasonic blade. The shield member is configured cover at least a first portion of the ultrasonic blade in the first position. The shield member is configured to uncover the first portion of the ultrasonic blade in the second position.

20 Claims, 41 Drawing Sheets

Related U.S. Application Data continuation of application No. 15/969,028, filed on May 2, 2018, now Pat. No. 10,716,957, which is a continuation of application No. 14/552,552, filed on Nov. 25, 2014, now Pat. No. 9,993,260.

(60) Provisional application No. 61/908,920, filed on Nov. 26, 2013.

(51) Int. Cl.
*A61B 17/00* (2006.01)
*A61B 17/28* (2006.01)
*A61B 18/00* (2006.01)
*A61B 18/14* (2006.01)
*A61B 90/00* (2016.01)

(52) U.S. Cl.
CPC ............... *A61B 2017/00353* (2013.01); *A61B 2017/2825* (2013.01); *A61B 2017/320071* (2017.08); *A61B 2017/320078* (2017.08); *A61B 2017/320084* (2013.01); *A61B 2017/320089* (2017.08); *A61B 2017/320093* (2017.08); *A61B 2017/320094* (2017.08); *A61B 2018/00011* (2013.01); *A61B 2018/00107* (2013.01); *A61B 2018/0063* (2013.01); *A61B 18/1442* (2013.01); *A61B 2090/0436* (2016.02); *A61B 2090/0472* (2016.02)

(58) Field of Classification Search
CPC .......... A61B 2017/2829; A61B 2017/320084; A61B 2090/0436; A61B 2090/0472
See application file for complete search history.

(56) References Cited

U.S. PATENT DOCUMENTS 5,938,633 A 8/1999 Beaupre
5,980,510 A 11/1999 Tsonton et al.
6,056,735 A 5/2000 Okada et al.
6,193,709 B1 2/2001 Miyawaki et al.
6,325,811 B1 12/2001 Messerly
6,358,267 B1 3/2002 Murakami et al.
6,500,176 B1 12/2002 Truckai et al.
6,669,690 B1 12/2003 Okada et al.
6,773,444 B2 8/2004 Messerly
6,783,524 B2 8/2004 Anderson et al.
6,958,070 B2 10/2005 Witt et al.
7,066,936 B2 6/2006 Ryan
7,074,219 B2 7/2006 Levine et al.
7,112,201 B2 9/2006 Truckai et al.
7,125,409 B2 10/2006 Truckai et al.
7,169,146 B2 1/2007 Truckai et al.
7,186,253 B2 3/2007 Truckai et al.
7,189,233 B2 3/2007 Truckai et al.
7,220,951 B2 5/2007 Truckai et al.
7,223,267 B2 5/2007 Isola et al.
7,235,073 B2 6/2007 Levine et al.
7,309,849 B2 12/2007 Truckai et al.
7,311,709 B2 12/2007 Truckai et al.
7,354,440 B2 4/2008 Truckai et al.
7,381,209 B2 6/2008 Truckai et al.
7,563,269 B2 7/2009 Hashiguchi
7,901,423 B2 3/2011 Stulen et al.
8,057,498 B2 11/2011 Robertson
8,328,834 B2 12/2012 Isaacs et al.
8,348,880 B2 1/2013 Messerly et al.
8,444,663 B2 5/2013 Houser et al.
8,444,664 B2 5/2013 Balanev et al.
8,461,744 B2 6/2013 Wiener et al.
8,523,889 B2 9/2013 Stulen et al.
8,535,257 B1 9/2013 Zelten et al.
8,591,459 B2 11/2013 Clymer et al.
8,591,536 B2 11/2013 Robertson
8,623,027 B2 1/2014 Price et al.
8,652,132 B2 2/2014 Tsuchiya et al.
8,662,745 B2 3/2014 Mishuchenko et al.
8,685,020 B2 4/2014 Weizman et al.
8,974,447 B2 3/2015 Kimball et al.
8,986,302 B2 3/2015 Aldridge et al.
9,005,199 B2 4/2015 Beckman et al.
9,023,071 B2 5/2015 Miller et al.
9,044,261 B2 6/2015 Houser
9,050,100 B2 6/2015 Yates et al.
9,084,878 B2 7/2015 Kawaguchi et al.
9,095,367 B2 8/2015 Olson et al.
9,113,943 B2 8/2015 Ross et al.
9,192,428 B2 11/2015 Houser et al.
9,283,045 B2 3/2016 Rhee et al.
9,375,230 B2 6/2016 Ross et al.
9,381,058 B2 7/2016 Houser et al.
9,393,037 B2 7/2016 Olson et al.
9,661,762 B2 5/2017 Katsuda
9,918,778 B2 3/2018 Walberg et al.
9,993,260 B2 6/2018 Stokes et al.
10,004,527 B2 6/2018 Gee et al.
10,004,528 B2 6/2018 Faller et al.
10,004,529 B2 6/2018 Stokes et al.
10,034,685 B2 7/2018 Boudreaux et al.
10,716,957 B2 7/2020 Stokes et al.
2005/0113828 A1* 5/2005 Shields .............. A61B 18/1445 606/51
2005/0192611 A1 9/2005 Houser
2005/0273126 A1 12/2005 Beaupre
2006/0079874 A1 4/2006 Faller et al.
2006/0265035 A1 11/2006 Yachi et al.
2007/0043297 A1* 2/2007 Miyazawa ......... A61B 18/1445 600/471
2007/0191713 A1 8/2007 Eichmann et al.
2007/0282333 A1 12/2007 Fortson et al.
2008/0200940 A1 8/2008 Eichmann et al.
2009/0030440 A1 1/2009 Mastri et al.
2010/0063525 A1 3/2010 Beaupre et al.
2010/0063527 A1 3/2010 Beaupre et al.
2010/0331873 A1 12/2010 Dannaher et al.
2012/0116265 A1 5/2012 Houser et al.
2012/0116433 A1* 5/2012 Houser .................. A61B 18/04 606/169
2012/0296334 A1* 11/2012 Kharin ..................... A61N 7/00 601/2
2013/0090576 A1 4/2013 Strulen et al.
2013/0103065 A1 4/2013 Timm et al.
2014/0012298 A1 1/2014 Cunningham et al.
2014/0012299 A1 1/2014 Stoddard et al.
2014/0135804 A1 5/2014 Weisenburgh, II et al.
2014/0180002 A1 6/2014 Voic
2015/0080924 A1 3/2015 Stulen et al.
2015/0080925 A1 3/2015 Schulte et al.
2016/0143657 A1 5/2016 Estera et al.
2016/0143659 A1 5/2016 Glutz et al.

FOREIGN PATENT DOCUMENTS

CN 101883529 A 11/2010
CN 203107225 U 8/2013
JP 2000-033092 A 2/2000
JP 2007-007140 A 1/2007
JP 2008-018226 A 1/2008
JP 2014-000311 A 1/2014
WO WO 2012/061739 A1 5/2012
WO WO 2012/116957 A1 9/2012
WO WO 2013/157571 A1 10/2013
WO WO 2013/183715 A1 12/2013
WO WO 2014/150169 A2 9/2014
WO WO 2013/062103 A1 4/2015
WO WO 2015/081038 A1 6/2015
WO WO 2015/081039 A1 6/2015

(56) References Cited

FOREIGN PATENT DOCUMENTS

| | | | |
|---|---|---|---|
| WO | WO 2015/081040 A1 | 6/2015 | |
| WO | WO 2015/081042 A1 | 6/2015 | |

OTHER PUBLICATIONS

Chinese Search Report dated Jan. 15, 2018 for Application No. CN 201480073943.5, 2 pgs.
Chinese Office Action, Notification of First Office Action, dated May 29, 2018 for Application No. CN 201480073956.2, 10 pgs.
Chinese Office Action, Notification of First Office Action, dated Feb. 24, 2018 for Application No. CN 201480074069.7, 12 pgs.
Chinese Search Report dated Feb. 7, 2018 for Application No. CN 201480074069.7, 2 pgs.
Chinese Office Action, Notification of First Office Action, dated Apr. 4, 2018 for Application No. CN 201480074070.X, 2 pgs.
Chinese Search Report dated Apr. 4, 2018 for Application No. CN 201480074070.X, 2 pgs.
Chinese Search Report dated May 17, 2018 for Application No. CN 201480073956.2, 3 pgs.
Chinese Supplemental Search Report dated Jan. 2, 2019 for Application No. CN 201480073943.5, 2 pgs.
European Communication dated Mar. 20, 2020, for Application No. 14812367.2, 6 pages.
European Communication dated May 4, 2020, for Application No. 14816009.6, 5 pages.
European Search Report and Written Opinion dated Jul. 22, 2020, for Application No. 20172910.0, 6 pages.
European Examination Report dated Nov. 16, 2020 for Application No. EP 14812367.2, 4 pgs.
European Examination Report dated Jul. 15, 2021 for Application No. EP 14812367.2, 4 pgs.
European Search Report and Written Opinion dated Sep. 30, 2021 for Application No. EP 21175501.2, 7 pgs.
European Examination Report dated Sep. 30, 2022 for Application No. EP 14812367.2, 4 pgs.
International Search Report and Written Opinion dated Jan. 30, 2015 for Application No. PCT/US2014/067221, 10 pgs.
International Search Report and Written Opinion dated Feb. 12, 2015 for Application No. PCT/US2014/067218, 9 pgs.
International Search Report and Written Opinion dated Feb. 12, 2015 for Application No. PCT/US2014/067219, 9 pgs.
International Search Report and Written Opinion dated Feb. 12, 2015 for Application No. PCT/US2014/067225, 9 pgs.
Japanese Office Action, Notification of Reasons for Refusal, dated Aug. 22, 2018 for Application No. JP 2016-534204, 5 pgs.
Japanese Search Report dated Aug. 22, 2018 for Application No. JP 2016-534204, 12 pgs.
Japanese Office Action, Notification of Reasons for Refusal, dated Jun. 26, 2018 for Application No. JP 2016-534207, 5 pgs.
Japanese Search Report dated Jun. 26, 2018 for Application No. JP 2016-534207, 10 pgs.
Japanese Notification of Reasons for Refusal dated Aug. 24, 2018, for Application No. 2016-534210, 3 pages.
Japanese Notification of Reasons for Refusal dated Aug. 27, 2018, for Application No. 2016-534211, 4 pages.
U.S. Appl. No. 61/410,603, filed Nov. 5, 2010.
U.S. Appl. No. 61/908,920, filed Nov. 26, 2013.

* cited by examiner

SHIELDING FEATURES FOR ULTRASONIC BLADE OF A SURGICAL INSTRUMENT

PRIORITY

This application is a continuation of U.S. patent application Ser. No. 16/890,198, entitled "Shielding Features for Ultrasonic Blade of a Surgical Instrument," filed Jun. 2, 2020, published as U.S. Pat. Pub. No. 2020/0346045 on Nov. 5, 2020, issued as U.S. Pat. No. 11,801,399 on Oct. 31, 2023, which is a continuation of U.S. patent application Ser. No. 15/969,028, entitled "Shielding Features for Ultrasonic Blade of a Surgical Instrument," filed May 2, 2018, issued as U.S. Pat. No. 10,716,957 on Jul. 21, 2020, which is a continuation of U.S. patent application Ser. No. 14/552,552, entitled "Shielding Features for Ultrasonic Blade of a Surgical Instrument," filed Nov. 25, 2014, issued as U.S. Pat. No. 9,993,260 on Jun. 12, 2018, which claims priority to U.S. Provisional Patent App. No. 61/908,920, entitled "Heat Management for Ultrasonic Surgical Instrument," filed Nov. 26, 2013, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. pat. app. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, now U.S. Pat. No. 9,393,037, issued Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
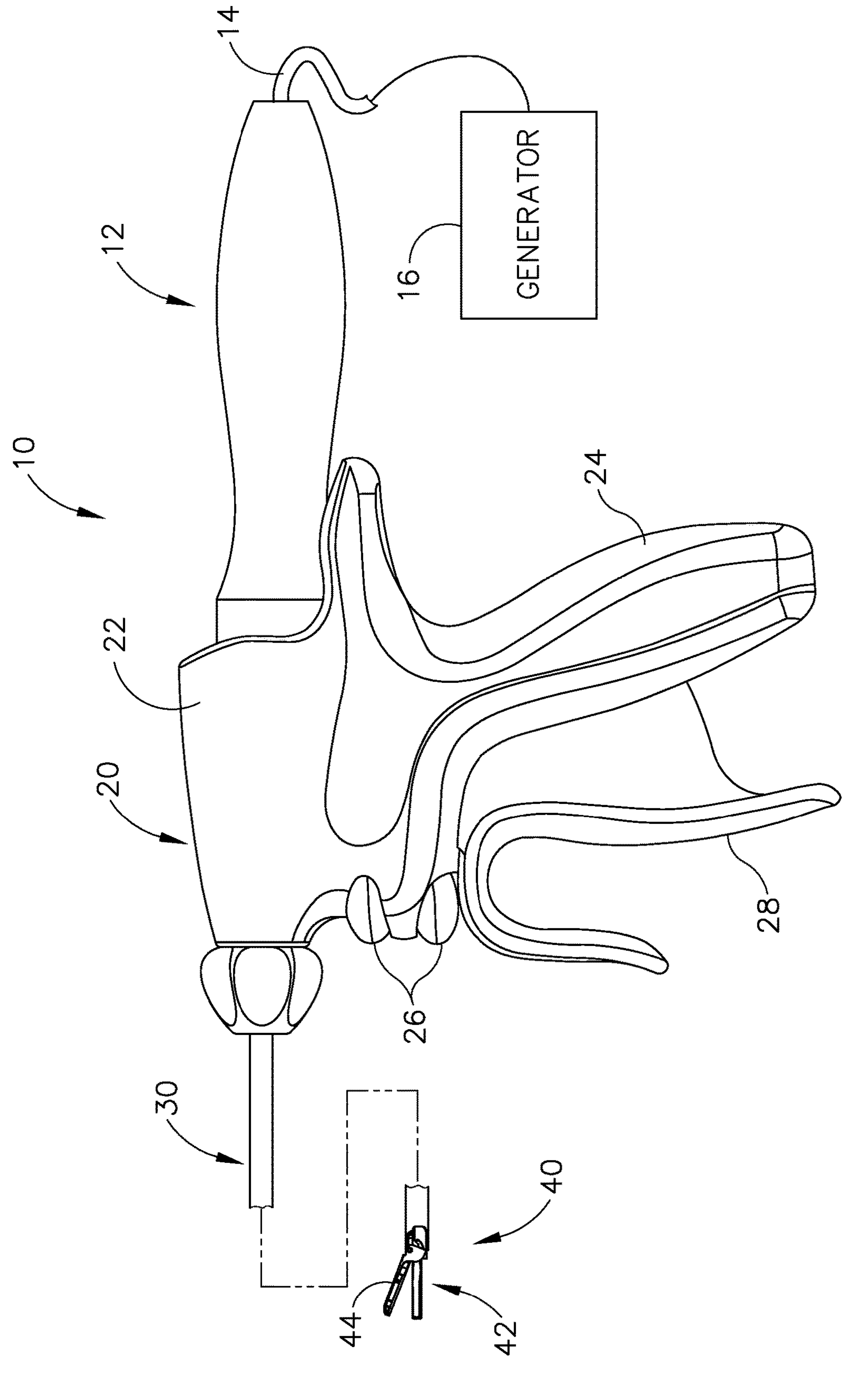
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIGS. 1-6B illustrate exemplary ultrasonic surgical instruments (10, 100). At least part of each instrument (10, 100) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750, now U.S. Pat. No. 8,623,027; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265; U.S. Pub. No. 2014/0005701, now U.S. Pat. No. 9,393,037; U.S. Pub. No. 2014/0114334, now U.S. Pat. No. 9,095,367; U.S. pat. app. No. 61/410,603; and/or U.S. patent application Ser. No. 14/028,717, published as U.S. Pub. No. 2015/0080924 on Mar. 19, 2015, issued as U.S. Pat. No. 10,172,636 on Jan. 8, 2019. The disclosures of each of the foregoing patents, publications, and applications are incorporated by reference herein. As described therein and as will be described in greater detail below, each instrument (10, 100) is operable to cut tissue and seal or weld tissue (e.g., a blood vessel, etc.) substantially simultaneously. It should also be understood that instruments (10, 100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instruments (10, 100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instruments (10, 100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
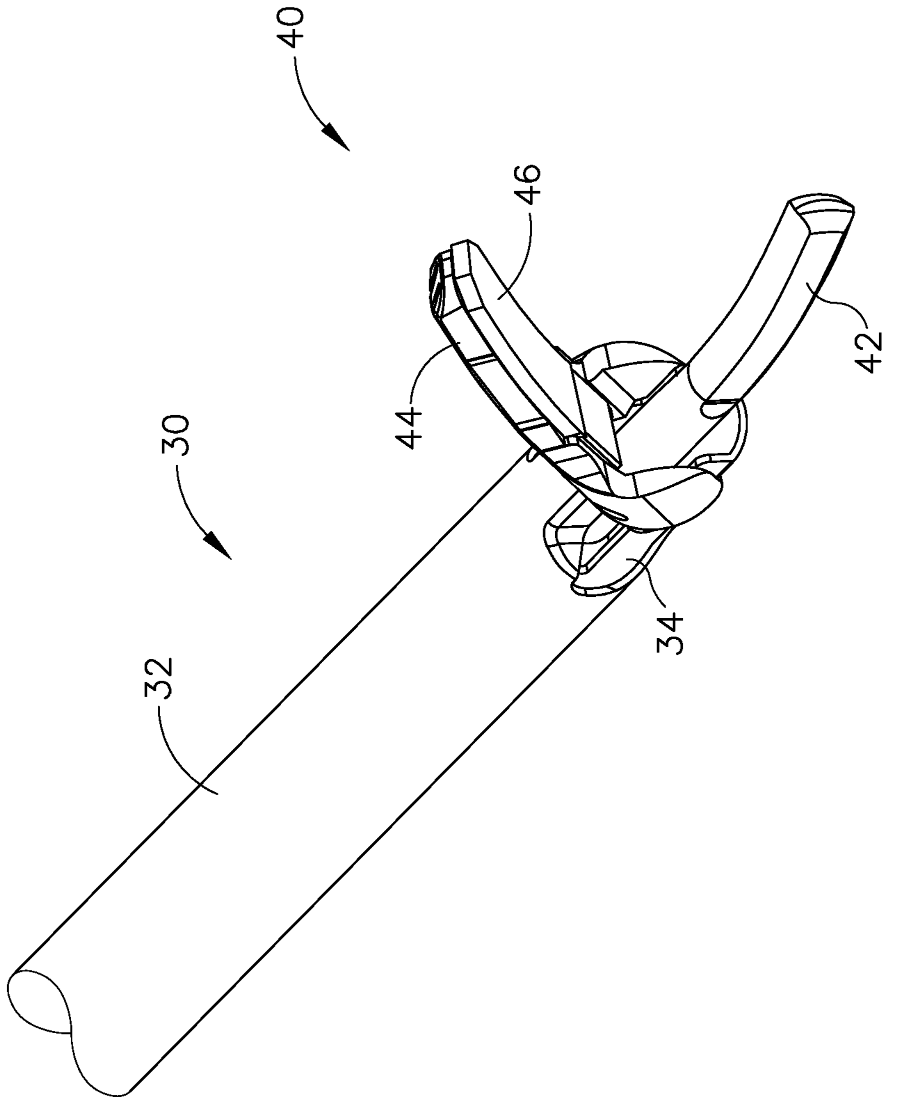
FIG. 2 depicts a perspective view of the end effector of the instrument of FIG. 1, in an open configuration.

A. Exemplary Ultrasonic Surgical Instrument for Minimally Invasive Surgical Procedures FIG. 1 illustrates an exemplary ultrasonic surgical instrument (10) that is configured to be used in minimally invasive surgical procedures (e.g., via a trocar or other small diameter access port, etc.). Instrument (10) of this example comprises a handle assembly (20), a shaft assembly (30), and an end effector (40). As shown in FIGS. 2-3B, shaft assembly (30) comprises an outer sheath (32), an inner tube (34) slidably disposed within outer sheath (32), and a waveguide (38) disposed within inner tube (34). As will be discussed in more detail below, longitudinal translation of inner tube (34) relative to outer sheath (32) causes actuation of clamp arm (44) at end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. In the present example, a resilient member biases trigger (28) away from pistol grip (24). Trigger (28) is pivotable toward pistol grip (24) to drive inner tube (34) proximally relative to outer sheath (32). When trigger (28) is thereafter released or driven away from pistol grip (24), inner tube (34) is driven distally relative to outer sheath (32). By way of example only, trigger (28) may be coupled with inner tube (34) in accordance with the teachings of various references cited herein. Other suitable ways in which trigger (28) may be coupled with inner tube (34) will be apparent to those of ordinary skill in the art in view of the teachings herein.

Figure 3A:
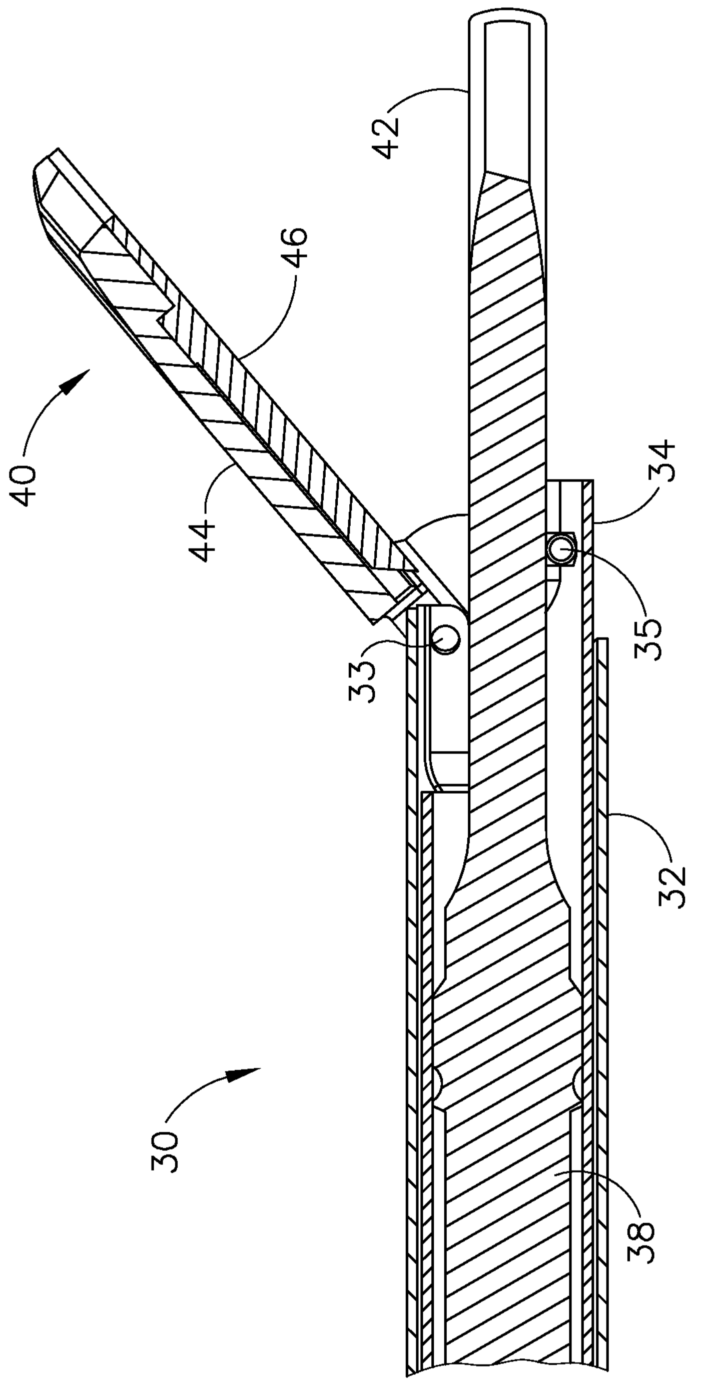
FIG. 3A depicts a side cross-sectional view of the end effector of FIG. 2, in the open configuration.
Figure 3B:
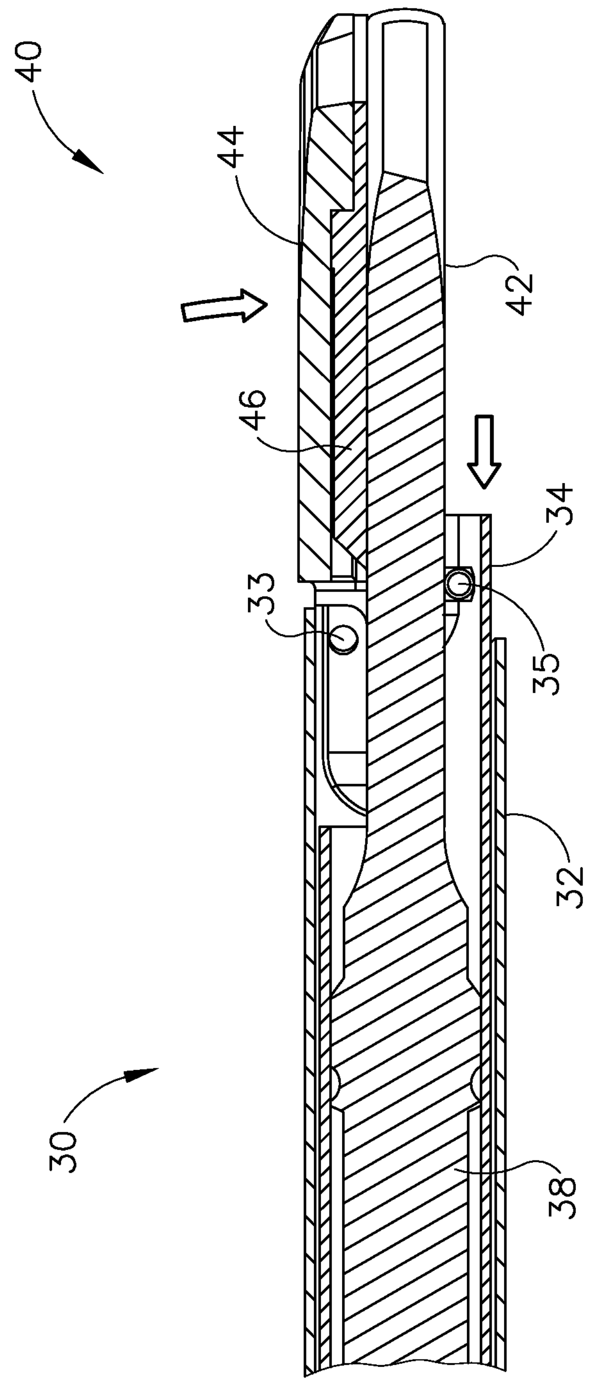
FIG. 3B depicts a side cross-sectional view of the end effector of FIG. 2, in a closed configuration.

As shown in FIGS. 2-3B, end effector (40) includes an ultrasonic blade (42) and a pivoting clamp arm (44). Clamp arm (44) includes a clamp pad (46) facing ultrasonic blade (42). Clamp arm (44) is pivotably coupled with a distal end of outer sheath (32) of shaft assembly (30), above ultrasonic blade (42), via a pin (33). A distal end of inner tube (34) is pivotably coupled with a proximal end of clamp arm (44), below ultrasonic blade (42), via another pin (35). Thus, longitudinal translation of inner tube (34) relative to outer sheath (32) causes clamp arm (44) to pivot about pin (33) toward and away from ultrasonic blade (42) to thereby clamp tissue between clamp pad (46) and ultrasonic blade (42) to transect and/or seal the tissue. In particular, as seen in the transition from FIG. 3A to FIG. 3B, proximal longitudinal translation of inner tube (34) relative to outer sheath (32) and handle assembly (20) causes clamp arm (44) to pivot toward ultrasonic blade (42); and distal longitudinal translation of inner tube (34) relative to outer sheath (32) and handle assembly (20) causes clamp arm (44) to pivot away from ultrasonic blade (42). It should therefore be understood that pivoting of trigger (28) toward pistol grip (24) will cause clamp arm (44) to pivot toward ultrasonic blade (42); and that pivoting of trigger (28) away from pistol grip (24) will cause clamp arm (44) to pivot away from ultrasonic blade (42).

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (38), which extends through shaft assembly (30) to reach ultrasonic blade (42). Waveguide (38) is secured within shaft assembly (30) via a pin (not shown), which passes through waveguide (38) and shaft assembly (30). This pin is located at a position along the length of waveguide (38) corresponding to a node associated with resonant ultrasonic vibrations communicated through waveguide (38). As noted above, when ultrasonic blade (42) is in an activated state (i.e., vibrating ultrasonically), ultrasonic blade (42) is operable to effectively cut through and seal tissue, particularly when the tissue is being clamped between clamp pad (46) and ultrasonic blade (42). It should be understood that waveguide (38) may be configured to amplify mechanical vibrations transmitted through waveguide (38). Furthermore, waveguide (38) may include features operable to control the gain of the longitudinal vibrations along waveguide (38) and/or features to tune waveguide (38) to the resonant frequency of the system.

In the present example, the distal end of ultrasonic blade (42) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (12) is energized, the distal end of ultrasonic blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (42) and clamp pad (46), the ultrasonic oscillation of ultrasonic blade (42) may simultaneously sever the tissue and denature the proteins in adjacent tissue cells, thereby providing a coagulative effect with relatively little thermal spread. In some versions, an electrical current may also be provided through ultrasonic blade (42) and/or clamp pad (46) to also seal the tissue.

An operator may activate buttons (26) to selectively activate transducer assembly (12) to thereby activate ultrasonic blade (42). In the present example, two buttons (26) are provided—one for activating ultrasonic blade (42) at a low power and another for activating ultrasonic blade (42) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb about pistol grip (24), position their middle, ring, and/or little finger about trigger (28), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265; U.S. Pub. No. 2014/0005701, now U.S. Pat. No. 9,393,037; and/or U.S. Pub. No. 2014/0114334, now U.S. Pat. No. 9,095,367. Additional merely illustrative variations for instrument (10) will be described in greater detail below. It should be understood that the below described variations may be readily applied to instrument (10) described above and any of the instruments referred to in any of the references that are cited herein, among others.

B. Exemplary Ultrasonic Surgical Instrument for Open Surgical Procedures

Figure 4:
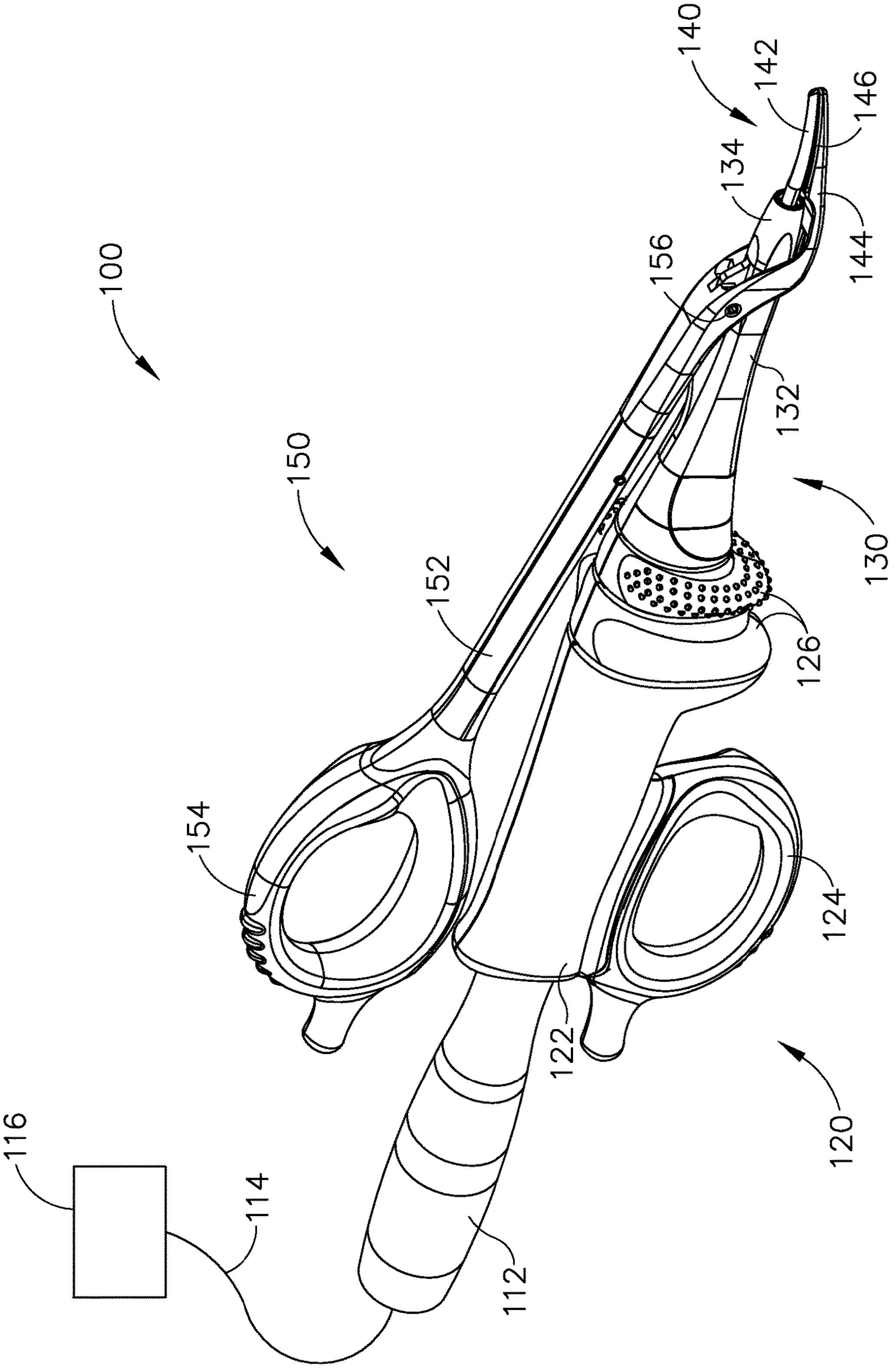
FIG. 4 depicts a perspective view of another exemplary surgical instrument.

FIG. 4 illustrates an exemplary ultrasonic surgical instrument (100) that is configured to be used in open surgical procedures. Instrument (100) of this example comprises a handle assembly (120), a shaft assembly (130), and an end effector (140). Handle assembly (120) comprises a body (122) including a finger grip ring (124) and a pair of buttons (126). Instrument (100) also includes a clamp arm assembly (150) that is pivotable toward and away from body (122). Clamp arm (150) includes a shank (152) with a thumb grip ring (154). Thumb grip ring (154) and finger grip ring (124) together provide a scissor grip type of configuration. It should be understood, however, that various other suitable configurations may be used, including but not limited to a pistol grip configuration.

Figure 5:
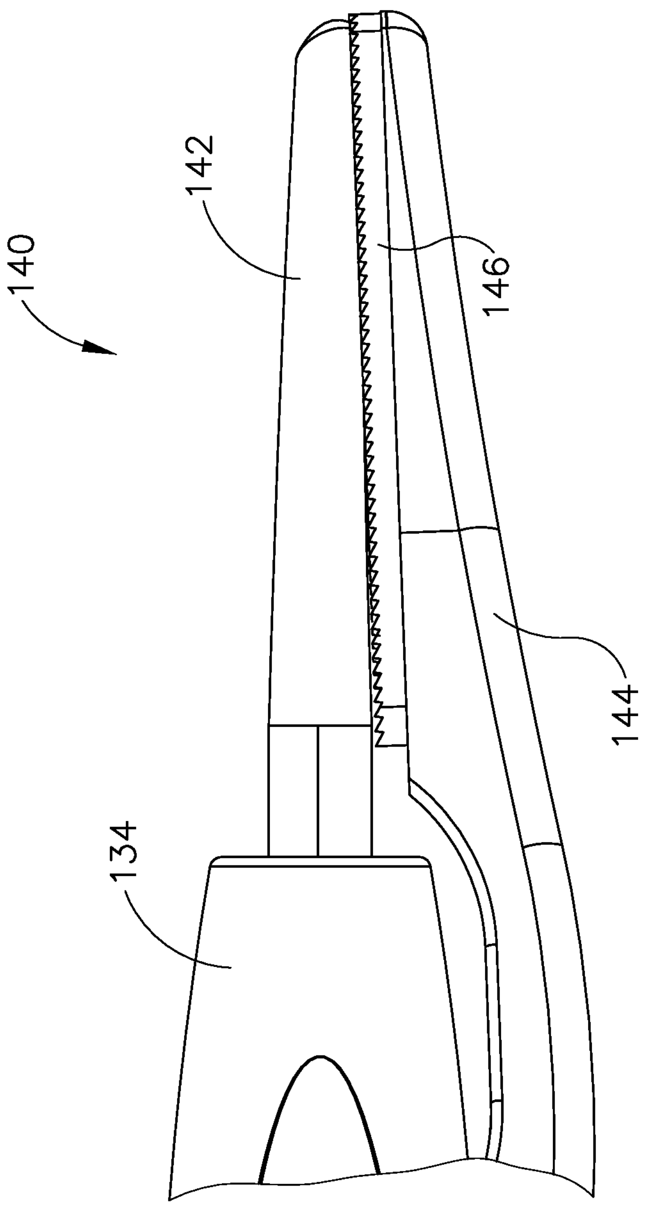
FIG. 5 depicts a side elevational view of the end effector of the instrument of FIG. 4, in a closed configuration.
Figure 6A:
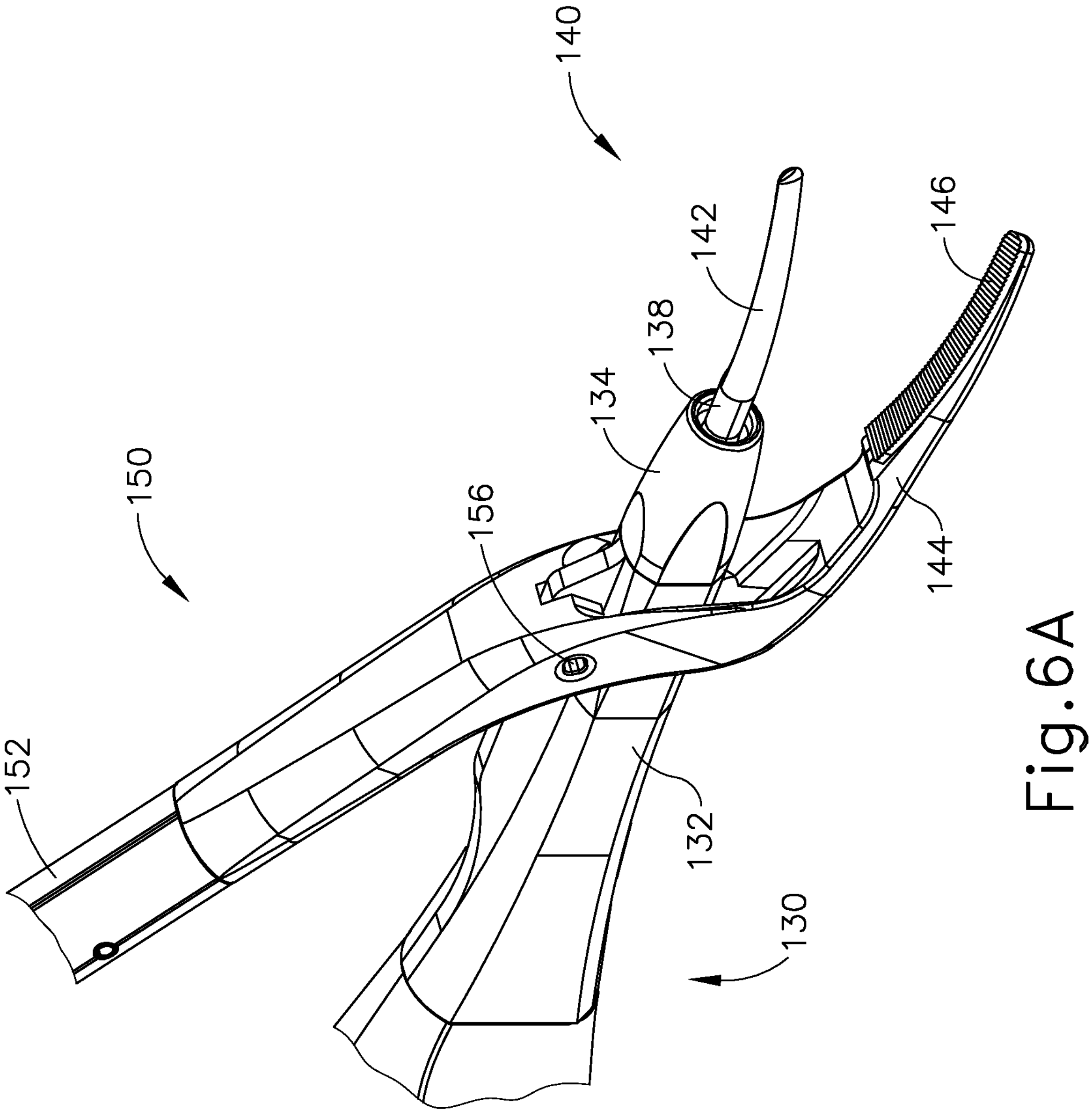
FIG. 6A depicts a perspective view of the end effector of FIG. 5, in an open configuration.
Figure 6B:
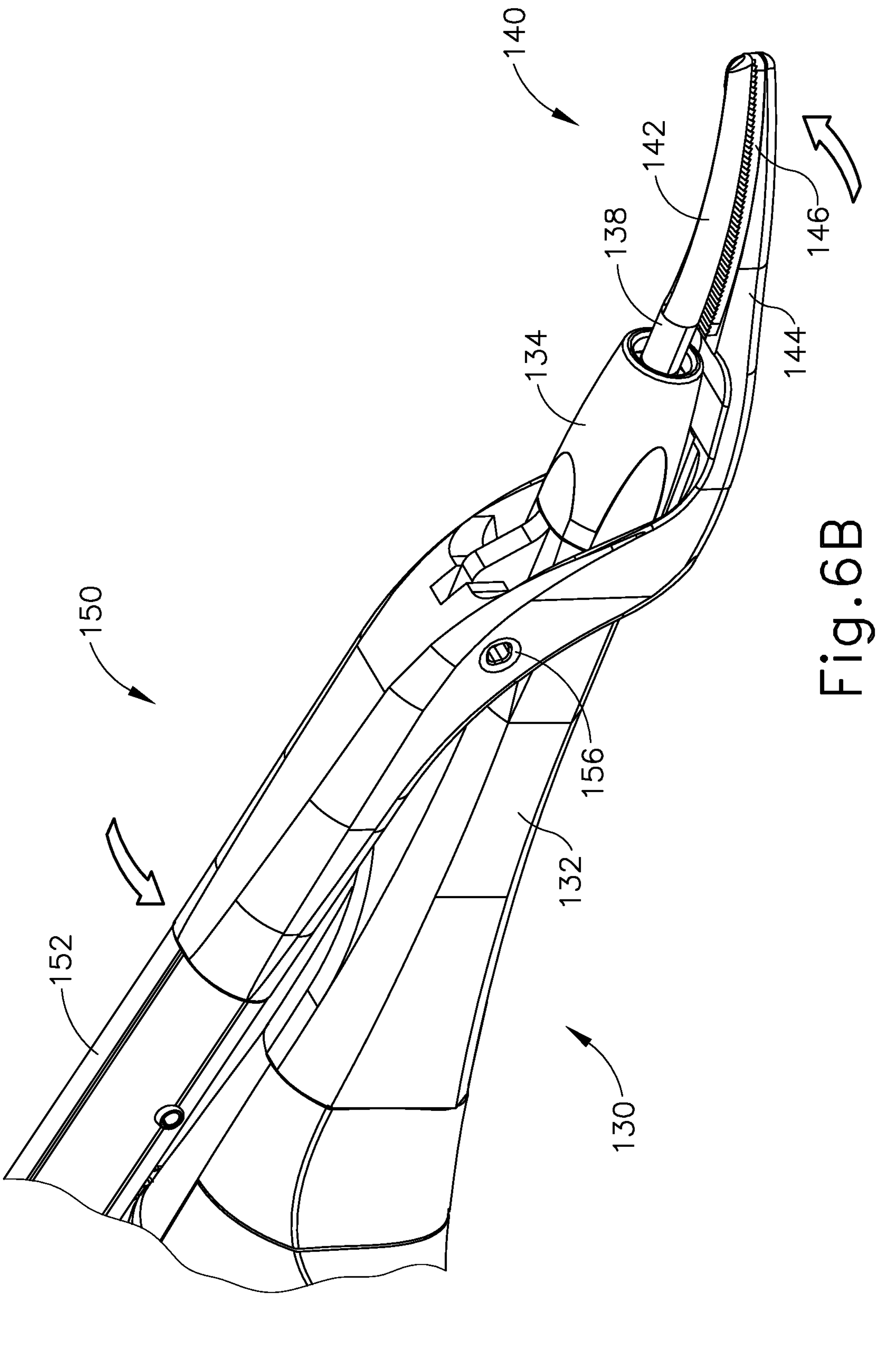
FIG. 6B depicts a perspective view of the end effector of FIG. 5, in a closed configuration.

Shaft assembly (130) comprises an outer sheath (132) extending distally from body (122). A cap (134) is secured to the distal end of sheath (132). As best seen in FIGS. 5-6B, end effector (140) comprises an ultrasonic blade (142) and a clamp arm (144). Ultrasonic blade (142) extends distally from cap (134). Clamp arm (144) is an integral feature of clamp arm assembly (150). Clamp arm (144) includes a clamp pad (146) facing ultrasonic blade (142). Clamp arm assembly (150) is pivotally coupled with outer sheath (132) via a pin (156). Clamp arm (144) is positioned distal to pin (156); while shank (152) and thumb grip ring (154) are positioned proximal to pin (156). Thus, as shown in FIGS. 6A-6B, clamp arm (144) is pivotable toward and away from ultrasonic blade (142) based on pivoting of thumb grip ring (154) toward and away from body (122) of handle assembly (120). It should therefore be understood that an operator may squeeze thumb grip ring (154) toward body (122) to thereby clamp tissue between clamp pad (146) and ultrasonic blade (142) to transect and/or seal the tissue. In some versions, one or more resilient members are used to bias clamp arm (144) to the open position shown in FIG. 6A. By way of example only, such a resilient member may comprise a leaf spring, a torsion spring, and/or any other suitable kind of resilient member.

Referring back to FIG. 4, an ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Ultrasonic vibrations that are generated by transducer assembly (112) are communicated along an acoustic waveguide (138), which extends through shaft assembly (130) to reach ultrasonic blade (142). Waveguide (138) is secured within shaft assembly (130) via a pin (not shown), which passes through waveguide (138) and shaft assembly (130). This pin is located at a position along the length of waveguide (138) corresponding to a node associated with resonant ultrasonic vibrations communicated through waveguide (138). As noted above, when ultrasonic blade (142) is in an activated state (i.e., vibrating ultrasonically), ultrasonic blade (142) is operable to effectively cut through and seal tissue, particularly when the tissue is being clamped between clamp pad (146) and ultrasonic blade (142). It should be understood that waveguide (138) may be configured to amplify mechanical vibrations transmitted through waveguide (138). Furthermore, waveguide (138) may include features operable to control the gain of the longitudinal vibrations along waveguide (138) and/or features to tune waveguide (138) to the resonant frequency of the system.

In the present example, the distal end of ultrasonic blade (142) is located at a position corresponding to an anti-node associated with resonant ultrasonic vibrations communicated through waveguide (138), in order to tune the acoustic assembly to a preferred resonant frequency $f_o$ when the acoustic assembly is not loaded by tissue. When transducer assembly (112) is energized, the distal end of ultrasonic blade (142) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (142) and clamp pad (46), the ultrasonic oscillation of ultrasonic blade (142) may simultaneously sever the tissue and denature the proteins in adjacent tissue cells, thereby providing a coagulative effect with relatively little thermal spread. In some versions, an electrical current may also be provided through ultrasonic blade (142) and/or clamp pad (146) to also seal the tissue.

An operator may activate buttons (126) to selectively activate transducer assembly (112) to thereby activate ultrasonic blade (142). In the present example, two buttons (126) are provided—one for activating ultrasonic blade (142) at a low power and another for activating ultrasonic blade (142) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb in thumb grip ring (154), position their ring finger in finger grip ring (124), position their middle finger about body (122), and manipulate buttons (126) using their index finger. Of course, any other suitable techniques may be used to grip and operate instrument (100); and buttons (126) may be located at any other suitable positions.

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265; U.S. Pub. No. 2014/0005701, now U.S. Pat. No. 9,393,037; U.S. Pub. No. 2014/0114334, now U.S. Pat. No. 9,095,367; and/or U.S. patent application Ser. No. 14/031,665, published as U.S. Pub. No. 2015/0080925 on Mar. 19, 2015. Additional merely illustrative variations for instrument (100) will be described in greater detail below. It should be understood that the below described variations may be readily applied to instrument (100) described above and any of the instruments referred to in any of the references that are cited herein, among others.

II. Exemplary Features for Providing Heat Management in an Ultrasonic Surgical Instrument In some instances, one or more regions of instrument (10, 100) may heat up during extended operation of instrument (10, 100) in a surgical procedure. By way of example only, blade (42, 142), clamp arm (44, 144), and/or other portions of instrument (10, 100) may eventually heat up over time. Such heating may be caused by friction and/or other factors. To the extent that the heat is initially generated in one particular component of instrument (10, 100) (e.g., blade (42, 142) or clamp arm (44, 144), etc.), such heat may be gradually transmitted to other portions of instrument (10, 100). It may be desirable to minimize such heating and/or otherwise manage such heating in order to avoid having heated portions of instrument (10, 100) contact tissue that should not be heated. For instance, the operator may wish for end effector (40, 140) to be relatively cool when the operator wishes to use end effector (40, 140) to perform spreading blunt dissections and/or simple tissue grasping, etc. It may also be desirable to minimize heat and/or otherwise manage heat in a way that does not significantly increase the size or operability of instrument (10, 100). Several examples of how heating may be minimized and/or otherwise managed are described in greater detail below; while other examples will be apparent to those of ordinary skill in the art in view of the teachings herein.

In addition to the examples described below, it should be understood that one or more portions of instrument (10, 100) may include a thermal insulator or barrier coating (e.g., a thin coating of thermal insulator or barrier material with a very low thermal conductivity). An example of a thermal insulator or barrier coating is a nanocomposite (e.g., hydro-NM-oxide) in an acrylic resin suspension. An example of such a coating is NANSULATE® coating by Industrial Nanotech, Inc. of Naples, Florida. Additional merely illustrative examples of thermal insulator or barrier coatings include the following: EST 1711 by Ellison Surface Technologies, Inc. of Mason, Ohio; EST 1732 by Ellison Surface Technologies, Inc. of Mason, Ohio; EST 3030 by Ellison Surface Technologies, Inc. of Mason, Ohio; EST 1711+EST 3030 by Ellison Surface Technologies, Inc. of Mason, Ohio; Oxytech V by Techmetals, Inc. of Dayton, Ohio; Alumina Titania; Zirconium Oxide; Aluminum Oxide; and/or various other kinds of coatings, including combinations thereof.

A thermal insulator or barrier coating may be applied to various external surfaces of instrument (10, 100), such as regions of blade (42, 142) that are not intended to contact tissue, clamp arm (44, 144), clamp pad (46, 146), outer sheath (32, 132), cap (134), etc. In addition or in the alternative, such a coating may be applied to various internal surfaces of instrument (10, 100), such as surfaces in generator (16, 116), transducer assembly (12, 112), internal electronics components, etc. In addition to providing a thermal barrier or insulation, such a coating may serve as a corrosion barrier, fire block, etc. In the below examples that include various components that are added to or otherwise incorporated into variations of instrument (10, 100), the coating may also be applied to one or more regions of such components. Other suitable ways in which a thermal coating may be incorporated into instrument (10, 100) and variations thereof will be apparent to those of ordinary skill in the art in view of the teachings herein.

To the extent that any of the examples discussed below are shown and described in the context of a variation of one particular kind of instrument (10 or 100), it should be understood that the same teachings may be readily applied to the other kind of instrument (10 or 100). Each example described below should therefore not be viewed as only having applicability to either instrument (10) or instrument (100). Furthermore, it is contemplated that the teachings below may be readily applied to other kinds of instruments, not just variations of instruments (10, 100).

As will be described in greater detail below, one or more shielding features may be used to avoid direct contact between a hot portion of instrument (10, 100) and tissue (or other structures). A gap may be defined between the shielding feature and the corresponding hot portion of instrument (10, 100), to avoid or minimize communication of heat from the hot portion of instrument (10, 100) and the shielding feature. Such a gap may be filled with liquid, air or some other gas, a solid insulating material, and/or any other suitable kind of filler, including combinations thereof. It should also be understood that various kinds of structural features may be interposed between the hot portion of instrument (10, 100) and the shielding feature, including but not limited to a roughened surface, grooves, dimples, pimples, nubs, knurling, a honeycomb structure, etc. Such structural features may minimize transfer of heat from the hot portion of instrument (10, 100) and the shielding feature. Similarly, a shielding feature (and/or a hot feature of instrument (10, 100)) may include external surface structures such as a roughened surface, grooves, dimples, pimples, nubs, knurling, a honeycomb structure, etc., to minimize transfer of heat from the shielding feature (or hot feature) to adjacent tissue, etc. Various merely illustrative examples of shielding features will be described in greater detail below. Other suitable examples will be apparent to those of ordinary skill in the art in view of the teachings herein.

It should be understood that any of the shields described below may comprise a temperature sensitive material. For instance, such a temperature sensitive material may be configured to change color and/or otherwise change in appearance in response to changes in temperature. In some such examples, the shield may change color as the temperature of the blade (42, 142) that is adjacent to the shield increases. The shield may thus provide the operator with a visual indication of the thermal condition of blade (42, 142) and/or the rest of end effector (40, 140). Various suitable materials that may be used to provide such properties will be apparent to those of ordinary skill in the art in view of the teachings herein. By way of example only, such material may include Huntsman RenShape 7820.

In some versions, one or more of the shields described below comprises Polybenzimidazole-Polyetherketoneketone (PBI-PEKK). As another merely illustrative example, one or more of the shields described below may comprise Perfluoroalkoxy (PFA). In addition or in the alternative, any of the shields described herein may comprise glass-filled PFA; Polyamide-imide (PAI), such as TORLON; Thermoplastic Polyimide (TPI), such as EXTEM; Polyetherimide (PEI), such as ULTEM; carbon-filled PEI; Polyetheretherketone (PEEK); glass-filled Polyaryletherketone (PAEK); DSM Somos ProtoTherm 12120; and/or DSM Somos NanoTool. Still other suitable materials that may be used to form the shields described below will be apparent to those of ordinary skill in the art in view of the teachings herein. Similarly, various suitable methods for forming shields (e.g., injection molding, SLA, etc.) will be apparent to those of ordinary skill in the art in view of the teachings herein.

A. Exemplary Longitudinally Translating Blade Shield

Figure 7A:
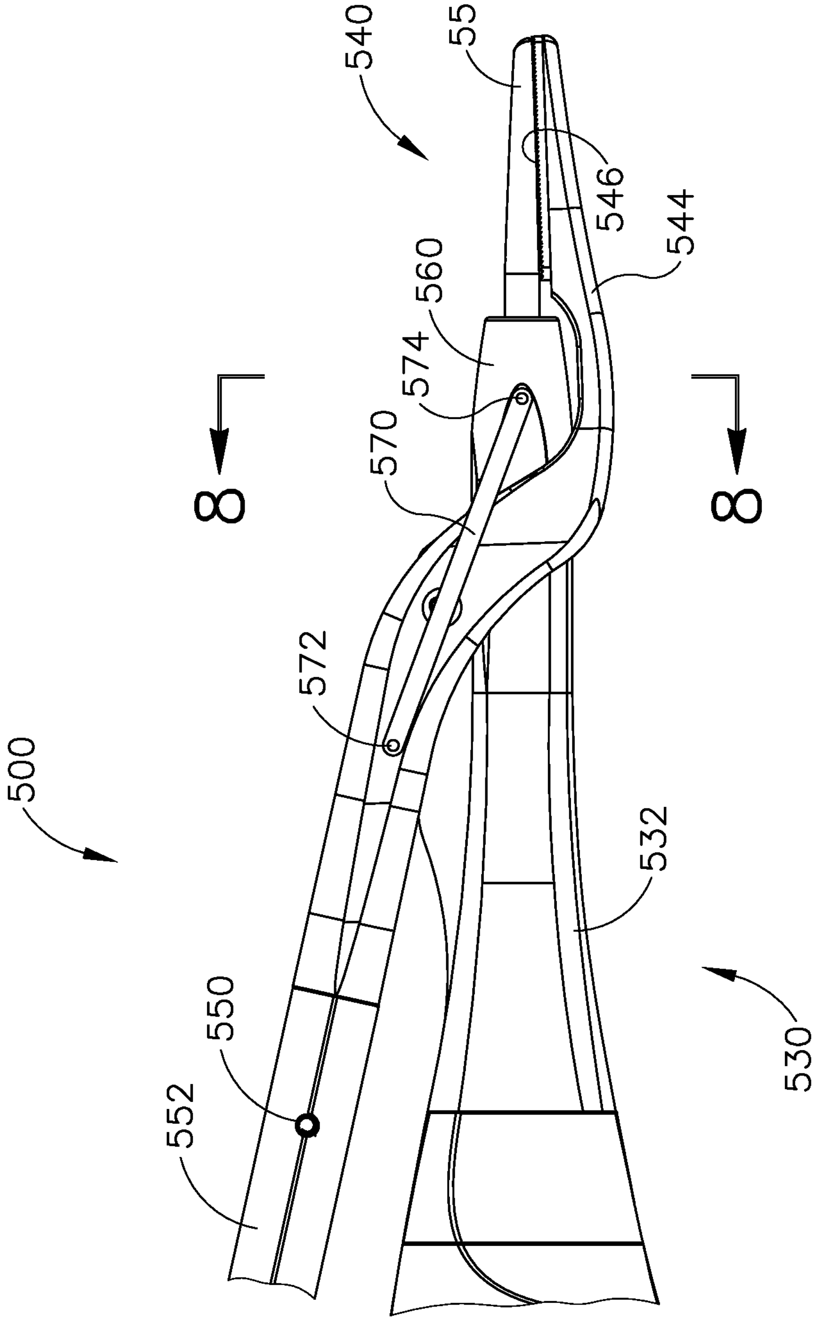
FIG. 7A depicts a side elevational view of the distal portion of an exemplary alternative surgical instrument, with a translating heat shield in a proximal position.
Figure 7B:
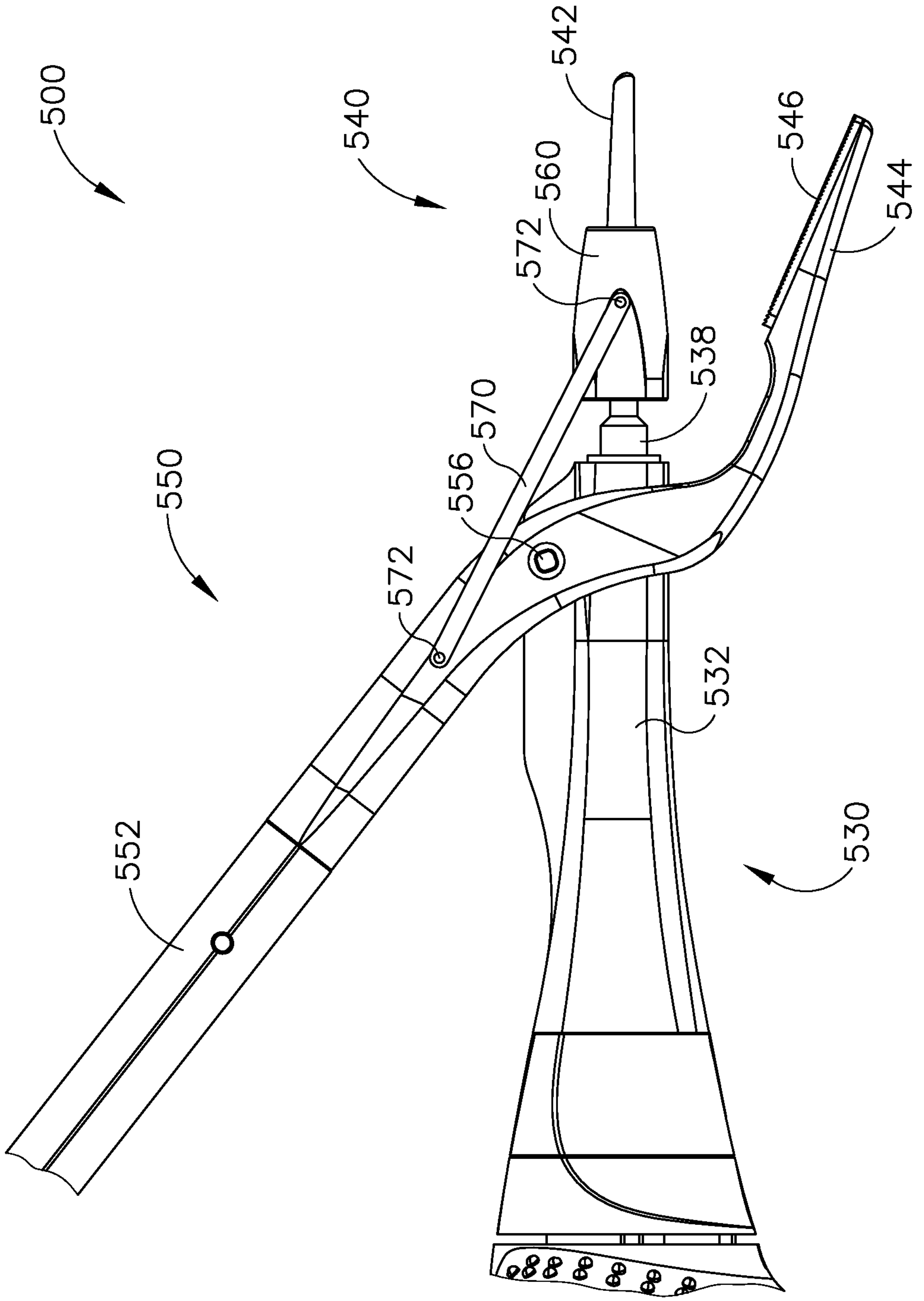
FIG. 7B depicts a side elevational view of the distal portion of the instrument of FIG. 7A, with the heat shield in a distal position.
Figure 8:
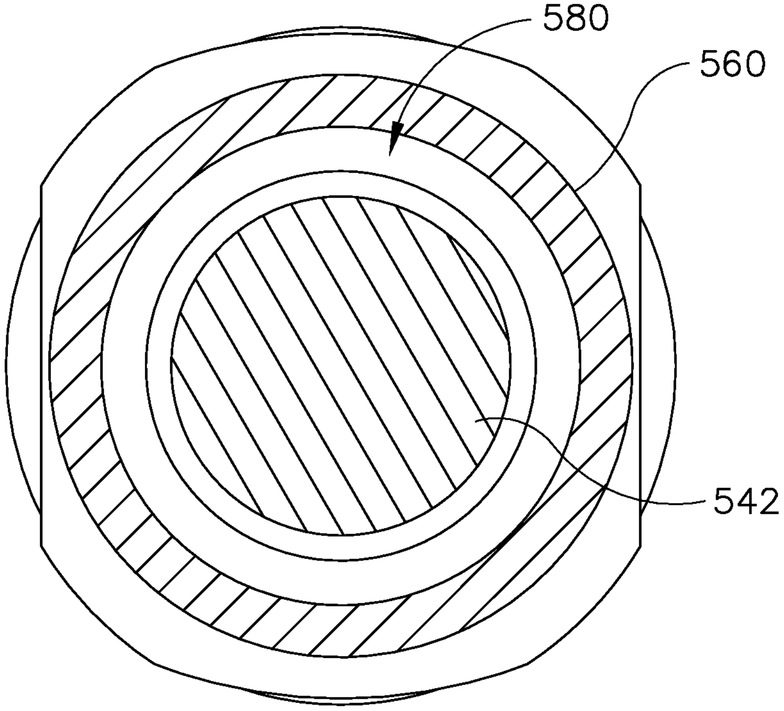
FIG. 8 depicts a cross-sectional end view of the heat shield of FIG. 7A positioned about the ultrasonic blade of the instrument of FIG. 7A.

FIGS. 7A-8 show the distal portion of an exemplary instrument (500) that includes a translating heat shield (560). Instrument (500) of this example is substantially similar to instrument (100) described above. In particular, instrument (500) of this example includes a shaft assembly (530), a clamp arm assembly (550), an ultrasonic blade (542), and a waveguide (538). Shaft assembly (530) includes an outer sheath (32) and heat shield (560). Clamp arm assembly (550) includes a shank (552) and a clamp arm (544) with a clamp pad (546). Clamp arm assembly (550) is pivotally coupled with outer sheath (532) via a pin (556). Thus, as shown in FIGS. 7A-7B, clamp arm (544) is pivotable toward and away from ultrasonic blade (542) based on pivoting of shank (552) toward and away from shaft assembly (530). It should be understood that gripping features similar to rings (124, 154) may be provided to facilitate pivotal movement of shank (552) relative to shaft assembly (530).

Instrument (500) of this example further includes a pivoting link (570). One end of pivoting link (570) is pivotally coupled with shank (552) via a pin (572), which is located generally proximally relative to pin (556). The other end of pivoting link (570) is pivotally coupled with heat shield (560) via a pin (574). It should be understood that pivoting link (570) is operable to drive heat shield (560) distally when shank (552) is pivoted away from shaft assembly (530), as shown in FIG. 7B; and retract shield (560) proximally when shank (552) is pivoted toward shaft assembly (530), as shown in FIG. 7A. As best seen in FIG. 8, heat shield (560) is configured to define a gap (580) between the inner surface of heat shield (560) and the outer surface of ultrasonic blade (542). This gap (580) prevents heat from being transferred from ultrasonic blade (542) to heat shield (560). Heat shield (560) thus remains substantially cool during operation of instrument (500), even if ultrasonic blade (542) heats up. By covering a portion of ultrasonic blade (542) when end effector (540) is in the open configuration as shown in FIG. 7B, heat shield (560) also substantially prevents tissue from directly contacting a substantial portion of ultrasonic blade (542).

In the present example, heat shield (560) just covers a portion of ultrasonic blade (542). It should be understood that heat shield (560) may be configured to cover more or less of ultrasonic blade (542) than is shown as being covered in FIG. 7B. It should also be understood that waveguide (538), blade (542), sheath (532), and/or some other portion of instrument (500) may include one or more rails and/or other structural features that provide support and guidance for heat shield (560) as heat shield (560) travels between proximal and distal positions. Such support/guidance structures may substantially maintain sizing and/or spacing in gap (580). Moreover, while air is positioned in gap (580) in the present example, it should be understood that any suitable substance or material may be positioned in gap (580). By way of example only, an absorbent pad that is saturated with a cooling fluid may be positioned in gap (580) to assist in cooling of ultrasonic blade (542) in accordance with the teachings herein. In addition or in the alternative, a wiping structure may be provided in gap (580) to assist in driving any surgical debris (e.g., coagulated blood, etc.) from the surface of ultrasonic blade (542). In some variations, shaft assembly (530) includes a collet feature that is coaxially positioned between heat shield (560) and blade (542). In some such versions, the collet feature is resiliently biased to assume an expanded configuration where the collet feature does not contact blade (542). When heat shield (560) is driven distally, heat shield engages a tapered portion of the collet and deforms the collet inwardly into engagement with blade (542). While the collet is in contact with the blade, the collet serves as a heat sink and thus draws heat away from blade (542). This drawn heat may be further transferred to shaft assembly (530). Still other suitable variations will be apparent to those of ordinary skill in the art in view of the teachings herein.

B. Exemplary Laterally Deflecting Blade Shield

Figure 9A:
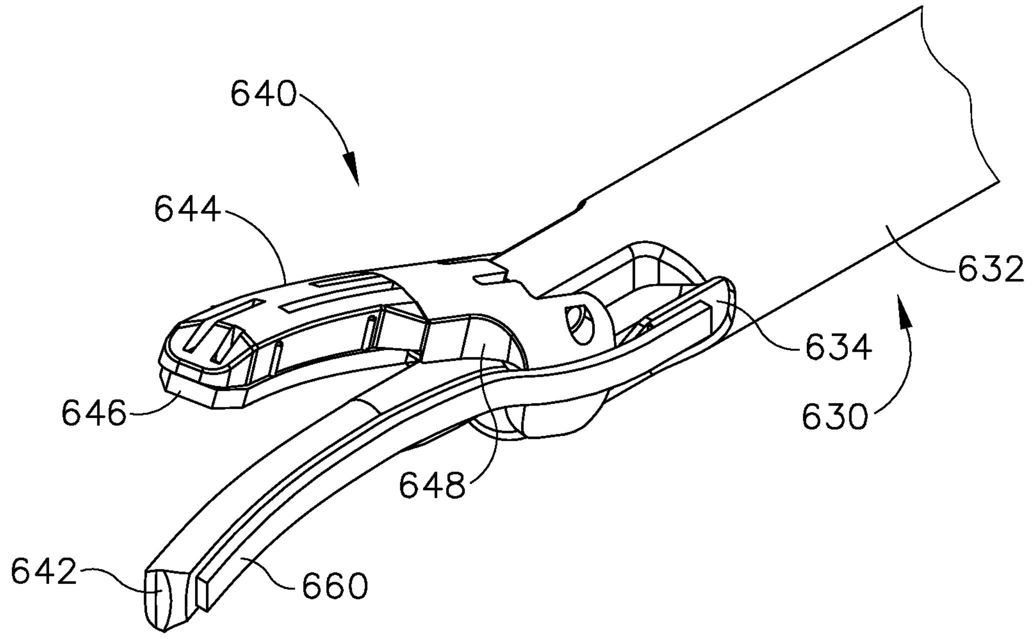
FIG. 9A depicts a perspective view of an exemplary alternative end effector, in an open configuration, with a heat shield engaging the ultrasonic blade.
Figure 9B:
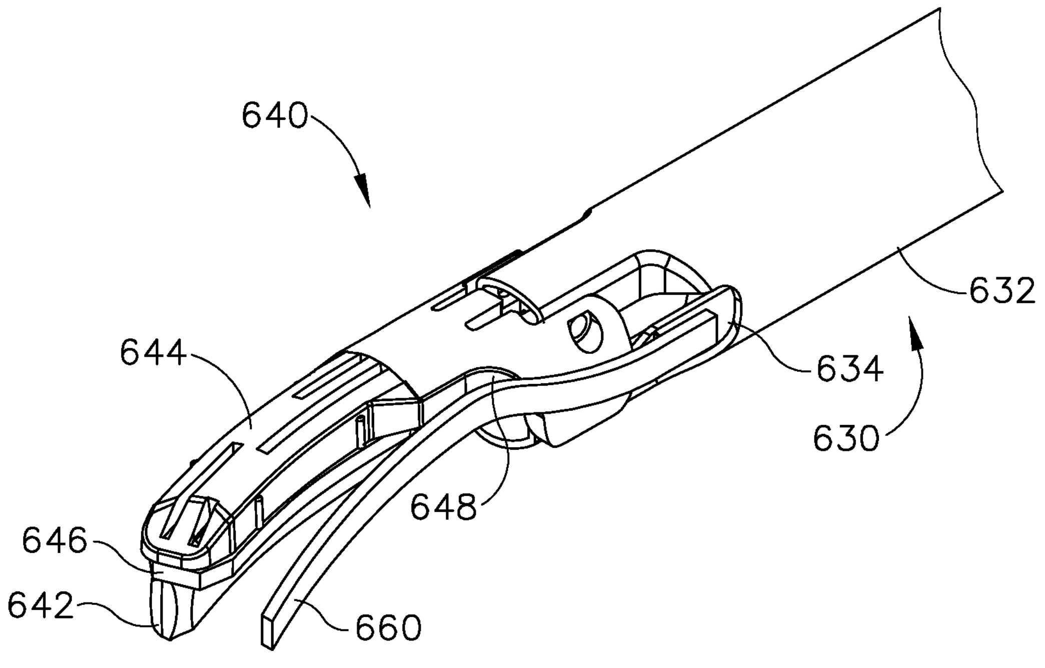
FIG. 9B depicts a perspective view of the end effector of FIG. 9A, in a closed configuration, with the heat shield deflected away from the ultrasonic blade.

FIGS. 9A-9B show an exemplary alternative end effector (640) that may be used in place of end effector (40). End effector (640) of this example is substantially similar to end effector (40) described above. In particular, end effector (640) includes an ultrasonic blade (642) and a pivoting clamp arm (644) with clamp pad (646). Shaft assembly (630) is substantially similar to shaft assembly (30) described above. In particular, shaft assembly (630) includes an outer sheath (632) and an inner tube (634). Clamp arm (644) is pivotally coupled with outer sheath (632) and with inner tube (634), such that clamp arm (644) pivots toward (FIG. 9B) and away from (FIG. 9A) blade (642) in response to translation of inner tube (634) relative to outer sheath (632).

End effector (640) of this example further includes a blade shield (660). The proximal end of blade shield (660) is secured to inner tube (634). Shield (660) is contoured to bend around a knuckle (648) of clamp arm (644) and complement the curvature of blade (642) when end effector (640) is in an open configuration as shown in FIG. 9A. In some versions, shield (660) contacts blade (642) when end effector (640) is in an open configuration as shown in FIG. 9A. When end effector (640) transitions to the closed configuration, knuckle (648) drives shield (660) outwardly away from blade (642) as shown in FIG. 9B. In the present example, shield (660) comprises a resilient material (e.g., metal, etc.), such that shield (660) returns back toward blade (642) when end effector (640) returns to the open configuration. Those of ordinary skill in the art will immediately recognize upon viewing FIGS. 9A-9B that clamp arm (644) travels along a first plane as clamp arm (644) moves toward and away from blade (642); while shield (660) travels along a second plane as shield (660) moves toward and away from blade (642), with the second plane being transverse to the first plane. Alternatively, these respective planes of travel may have any other suitable relationship.

Figure 10:
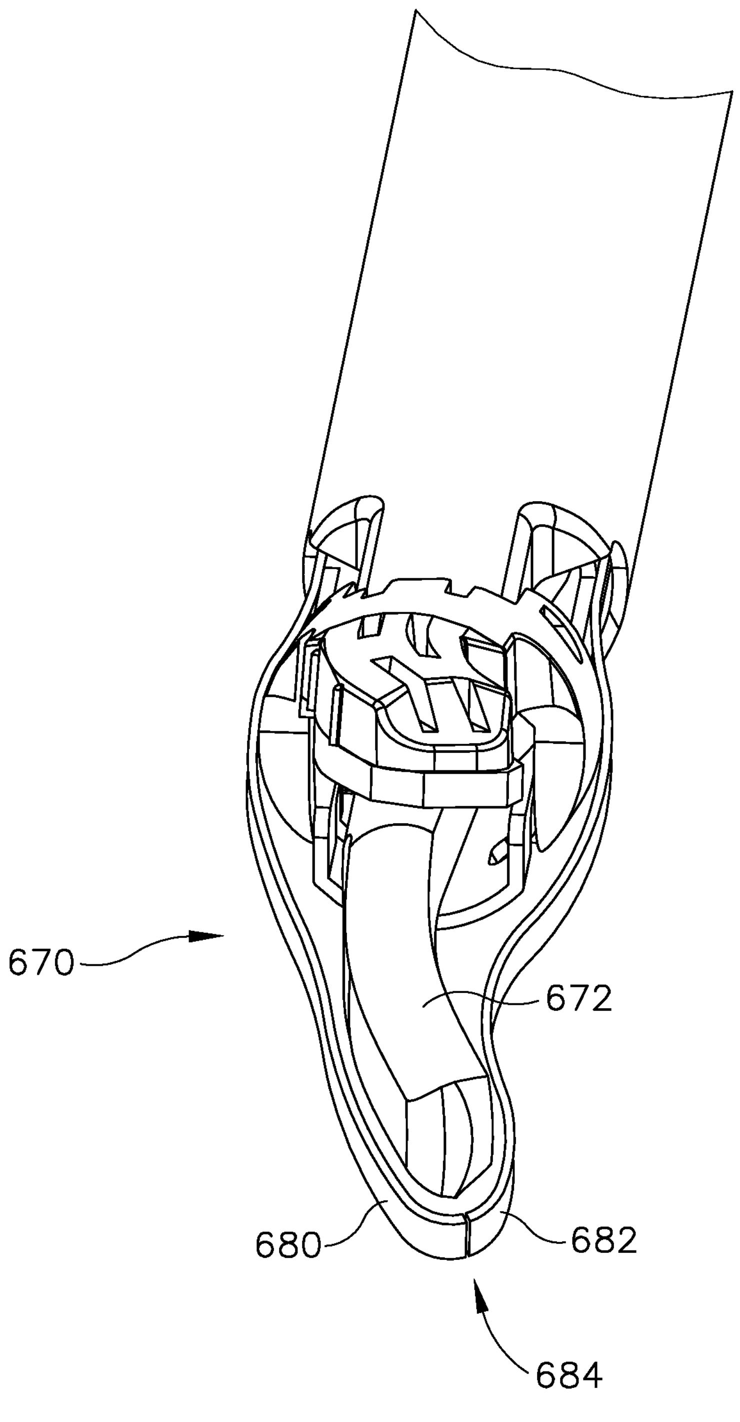
FIG. 10 depicts a perspective view of an exemplary alternative end effector, in an open configuration, with dual heat shields engaging the ultrasonic blade.

FIG. 10 shows yet an exemplary variation where an end effector (670) that is otherwise identical to end effector (640) includes a pair of shields (680, 682). Shields (680, 682) of this example are substantially similar to shield (660) except that shields (680, 682) of this example are on opposite lateral sides of blade (672) and wrap completely around blade (672). Shields (680, 682) meet at a seam (684) positioned distal to blade (672) when end effector (670) is in an open configuration. Shields (680 682) may deflect outwardly away from blade (672), spreading apart from each other, when end effector (670) is closed. In the present examples, shields (660, 680, 682) serve as a shield that prevents direct contact between tissue and at least a portion of blade (642). In addition or in the alternative, shields (660, 680, 682) may serve as a heat sink that draws heat away from blade (642, 672). It should also be understood that shields (660, 680, 682) may include an absorbent pad that is saturated with a cooling fluid. Such a pad may contact blade (642, 672) when end effector (640, 670) is in the open configuration and thereby cool blade (642, 672) in accordance with the teachings above. As yet another merely illustrative variation, shield (660, 680, 682) may include silicon tubing extending along at least a portion of the length of shield (660, 680, 682). As will be described in greater detail below, such silicon tubing may capture vapor plumes emitted during cutting/sealing of tissue by blade (642, 672) and/or other fluid from a surgical site. Such captured vapor plumes and/or other fluid from a surgical site may assist in cooling of shield (660, 680, 682) and/or blade (642). Other suitable variations will be apparent to those of ordinary skill in the art in view of the teachings herein.

C. Exemplary Stationary Blade Shield

Figure 11:
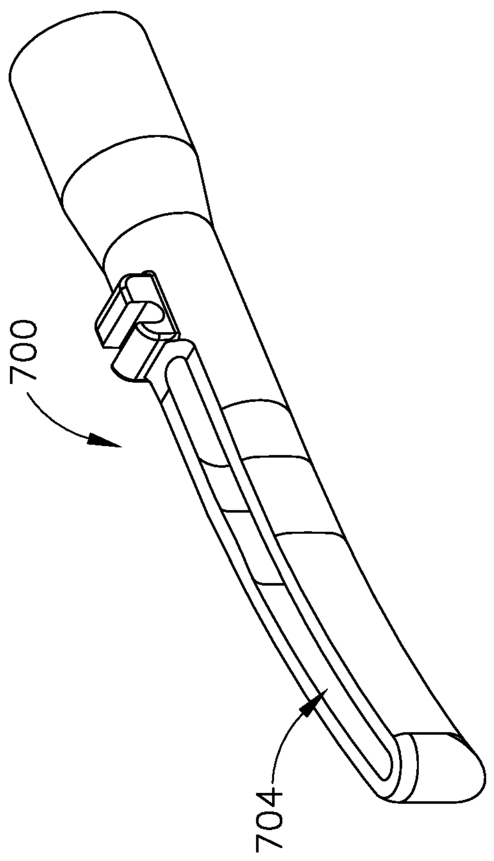
FIG. 11 depicts a perspective view of an exemplary ultrasonic blade shield.
Figure 12:
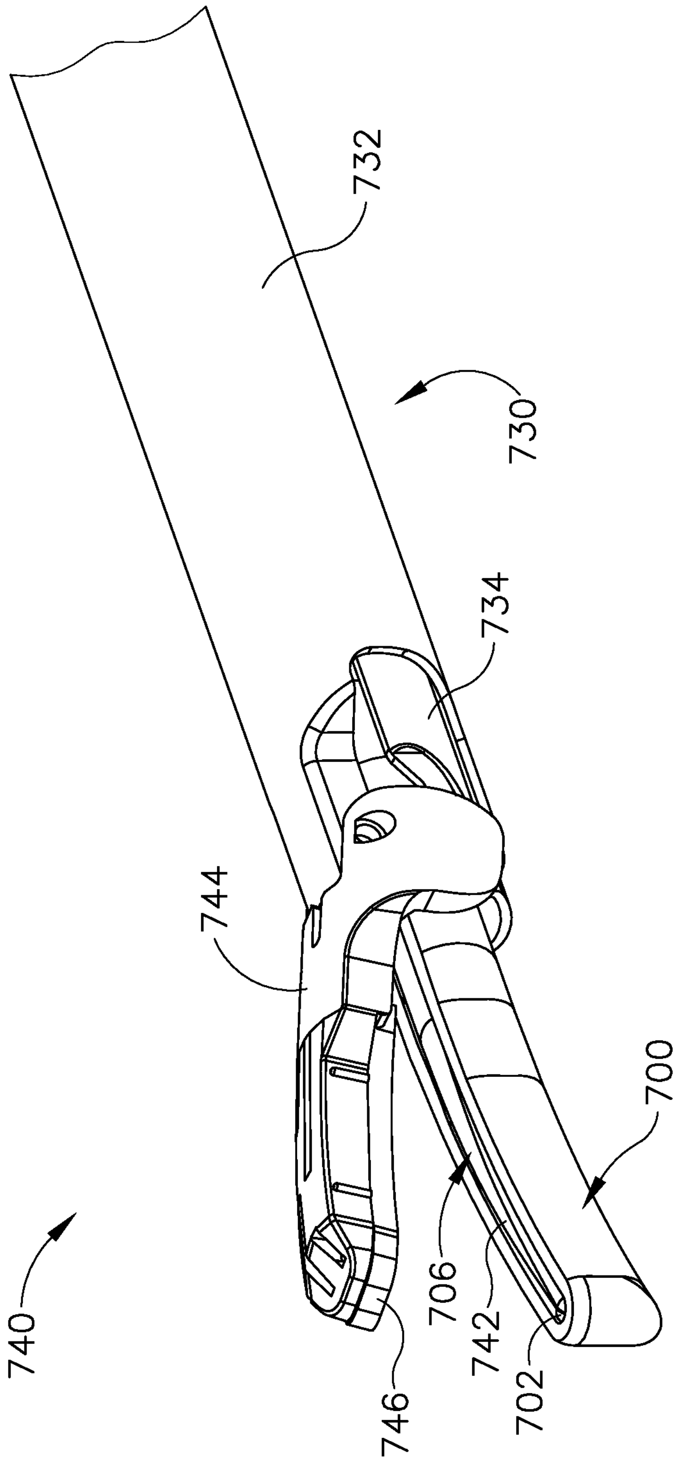
FIG. 12 depicts a perspective view of an end effector with the blade shield of FIG. 11 fitted on the ultrasonic blade.
Figure 13:
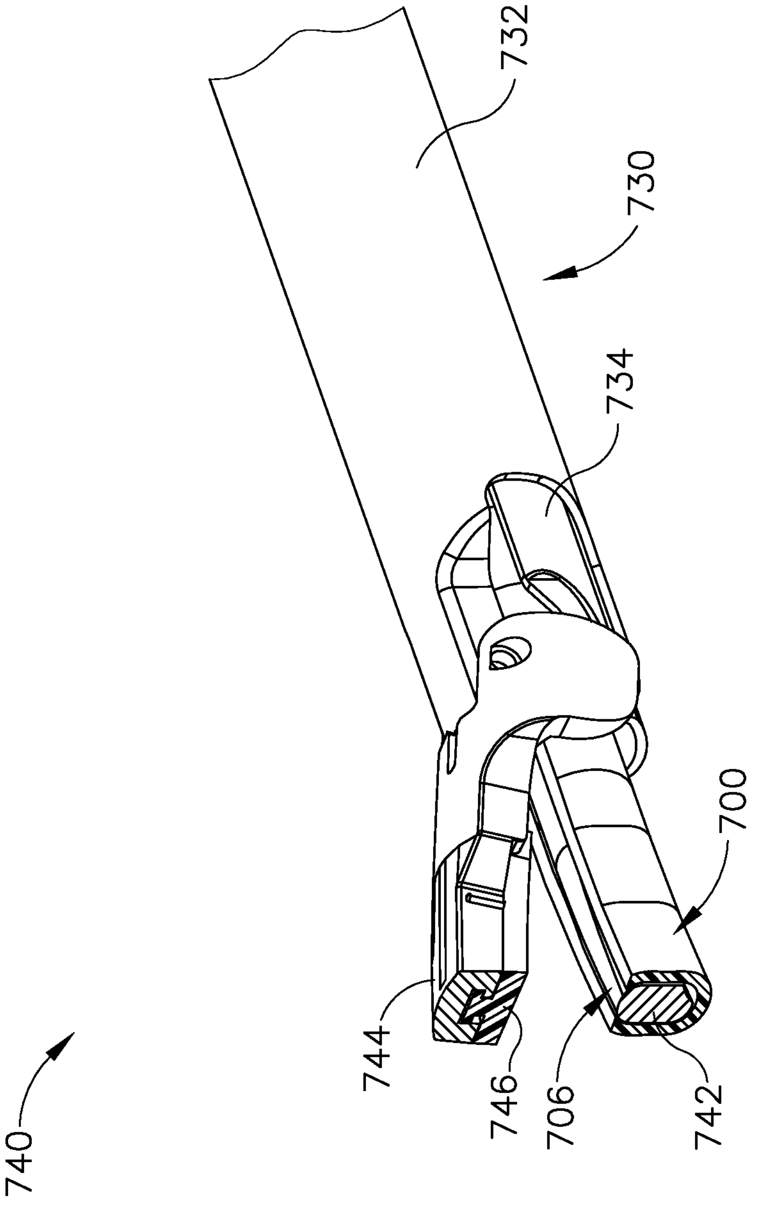
FIG. 13 depicts a perspective view of the end effector of FIG. 12, with a distal portion of the end effector shown in cross section.

FIGS. 11-13 depict an exemplary blade shield (700), which is fitted on a blade (742) of an end effector (740). End effector (740) of this example is substantially similar to end effector (40) described above. Shield (700) of the present example is formed of a thermally insulative material. By way of example only, shield (700) may comprise silicone, graphine, graphite, and/or any other suitable material(s). End effector (740) of this example is substantially similar to end effector (40) described above. In particular, end effector (740) includes an ultrasonic blade (742) and a pivoting clamp arm (744) with clamp pad (746). Shaft assembly (730) is substantially similar to shaft assembly (30) described above. In particular, shaft assembly (730) includes an outer sheath (732) and an inner tube (734). Clamp arm (744) is pivotally coupled with outer sheath (732) and with inner tube (734), such that clamp arm (744) pivots toward and away from blade (742) in response to translation of inner tube (734) relative to outer sheath (732). In the present example, the proximal end of shield (700) is compressed between the proximal end of blade (742) and the distal end of inner tube (734), such that shield (700) is held in place by pressure/friction. Alternatively, shield (700) may be secured by a bushing, by necking of inner tube (734), by crimping inner tube (734), by an adhesive, and/or using any other suitable structures/techniques as will be apparent to those of ordinary skill in the art in view of the teachings herein.

As shown, shield (700) of this example is fitted snugly about blade (742), covering the distal tip (702) of blade (742). However, shield (700) includes an opening (704) that leaves a clamping region (706) of blade (742) exposed. Thus, as clamp arm (744) is pivoted toward blade (742), blade (742) still cuts and seals tissue that is compressed between clamp pad (746) and clamping region (706) of blade (742) just like blade (42) described above. However, shield (700) prevents the rest of blade (742) from coming into direct contact with tissue. Shield (700) may thus prevent blade (742) from inadvertently damaging tissue when blade (742) gets hot during extended use of end effector (740). In some variations, a gap is defined between shield (700) and blade (742). Such a gap may receive vapor and/or fluid from the surgical site. Such vapor and/or fluid may assist in cooling blade (742). While shield (700) of the present example covers distal tip (702) of blade (742) it should be understood that shield (700) may instead distally terminate at any other suitable location in relation to distal tip (702). For instance, shield (700) may distally terminate at the longitudinal mid-region of blade (742), anywhere proximal to the longitudinal mid-region of blade (742), or anywhere distal to the longitudinal mid-region of blade (742). As another merely illustrative variation, shield (700) may be selectively retractable to selectively expose a distal region of blade (742) or even the full length of blade (742). Various suitable ways in which shield (700) may be selectively retracted and advanced will be apparent to those of ordinary skill in the art in view of the teachings herein.

Figure 14:
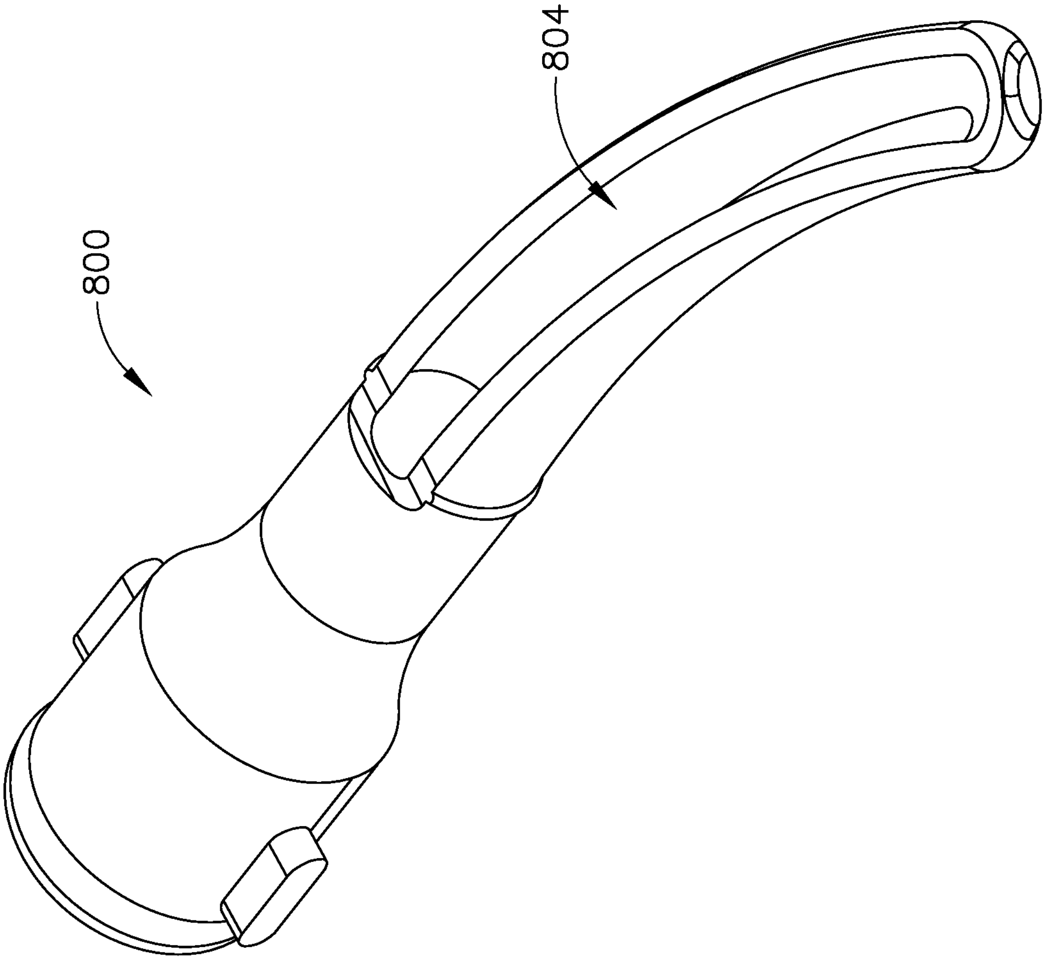
FIG. 14 depicts a perspective view of another exemplary alternative ultrasonic blade shied.
Figure 15:
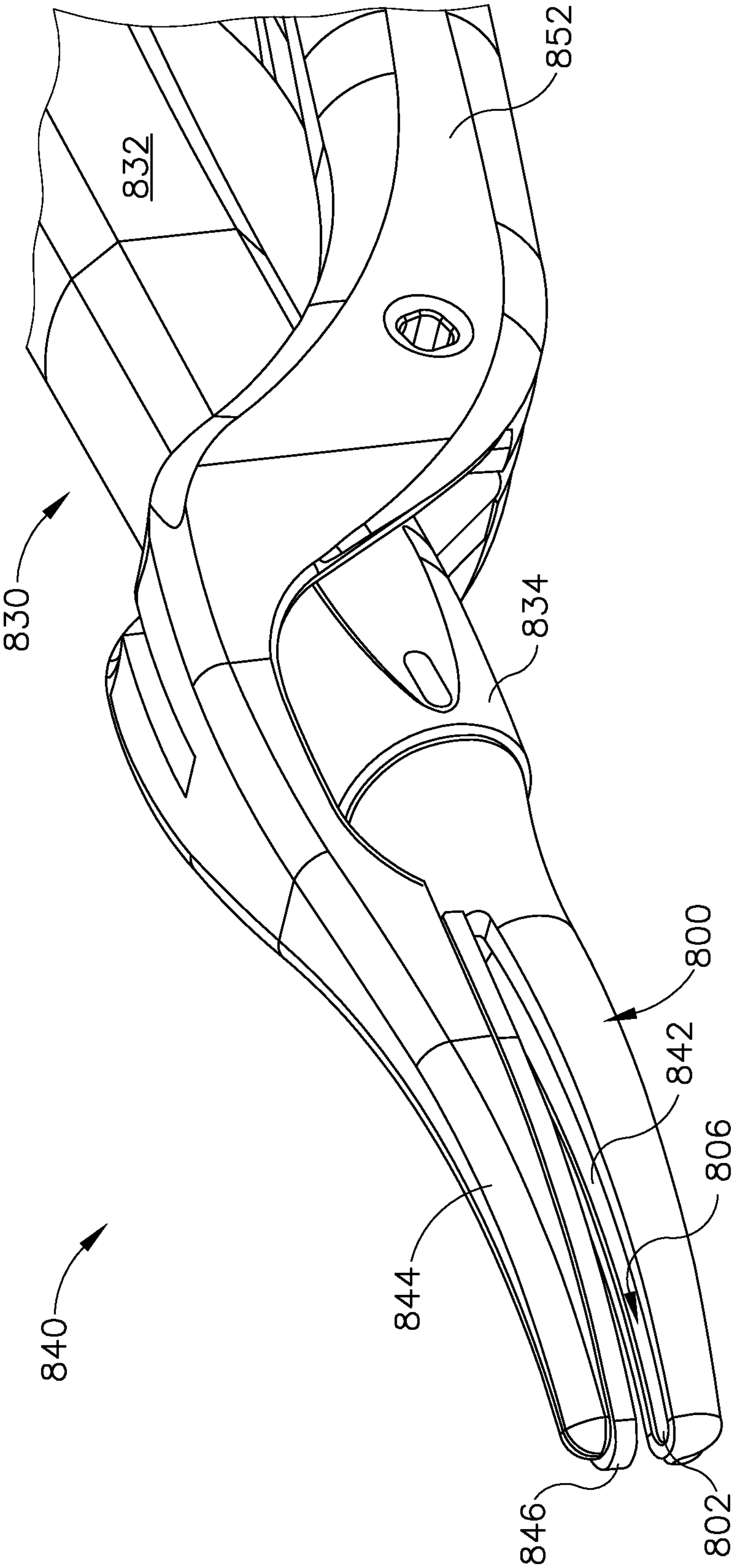
FIG. 15 depicts a perspective view of an end effector with the blade shield of FIG. 14 fitted on the ultrasonic blade.
Figure 16:
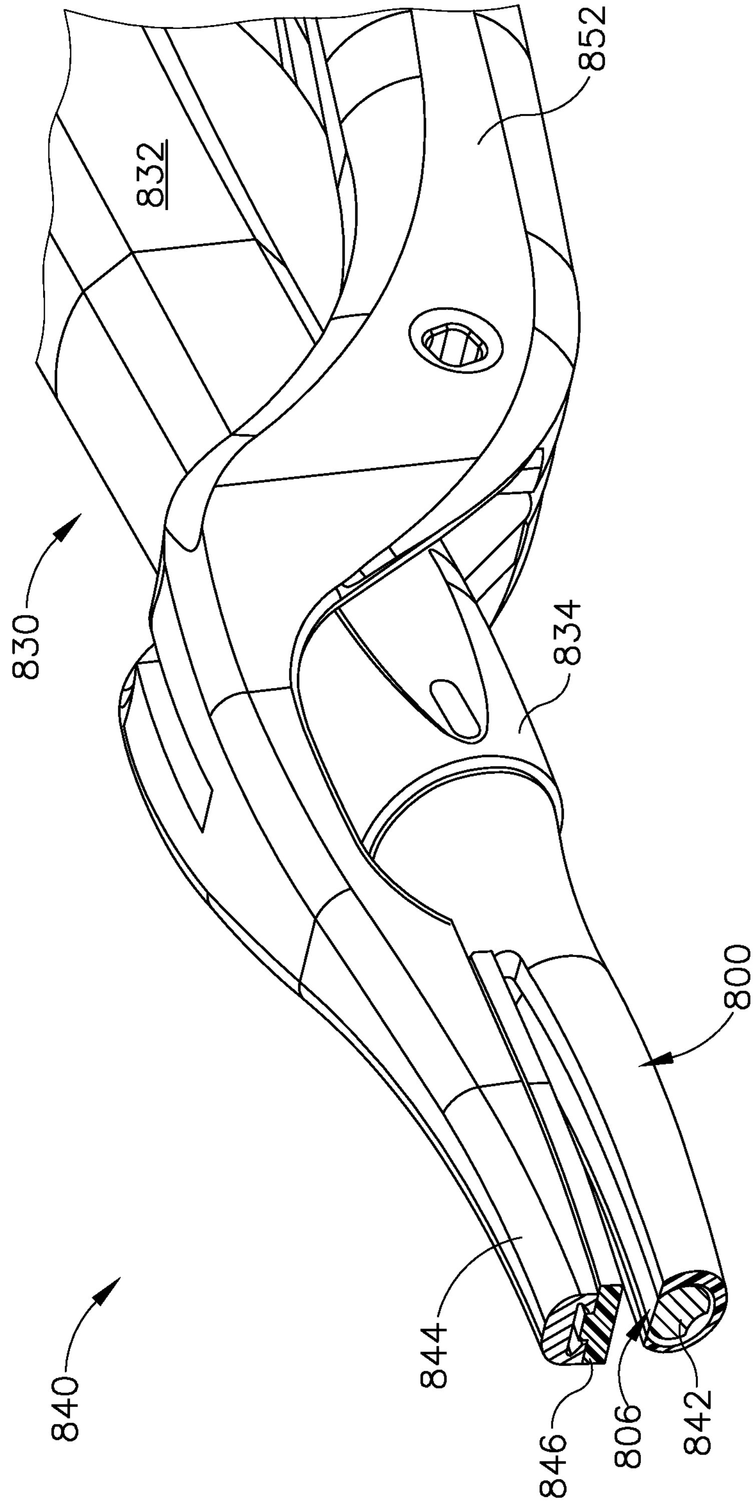
FIG. 16 depicts a perspective view of the end effector of FIG. 15, with a distal portion of the end effector shown in cross section.

FIGS. 14-16 depict another exemplary blade shield (800), which is fitted on a blade (842) of an end effector (840). Shield (800) of the present example is formed of a thermally insulative material. By way of example only, shield (800) may comprise silicone, graphine, graphite, and/or any other suitable material(s). End effector (840) of this example is substantially similar to end effector (140) described above. In particular, end effector (840) includes an ultrasonic blade (842) and a pivoting clamp arm (844) with clamp pad (846). Shaft assembly (830) is substantially similar to shaft assembly (130) described above. In particular, shaft assembly (830) includes an outer sheath (832) and a cap (834). Clamp arm (844) is integral with a shank (852), the combination of which is pivotally coupled with outer sheath (832) such that clamp arm (844) pivots toward and away from blade (842) in response to pivoting of shank (852) relative to shaft assembly (830). Shield (800) may be held in place similar to shield (700) as described above; and/or using any other suitable structures/techniques as will be apparent to those of ordinary skill in the art in view of the teachings herein.

As shown, shield (800) of this example is fitted snugly about blade (842), covering the distal tip (802) of blade (842). However, shield (800) includes an opening (804) that leaves a clamping region (806) of blade (842) exposed. Thus, as clamp arm (844) is pivoted toward blade (842), blade (842) still cuts and seals tissue that is compressed between clamp pad (846) and clamping region (806) of blade (842) just like blade (42) described above. However, shield (800) prevents the rest of blade (842) from coming into direct contact with tissue. Shield (800) may thus prevent blade (842) from inadvertently damaging tissue when blade (842) gets hot during extended use of end effector (840). In some variations, a gap is defined between shield (800) and blade (842). Such a gap may receive vapor and/or fluid from the surgical site. Such vapor and/or fluid may assist in cooling blade (842). While shield (800) of the present example covers distal tip (802) of blade (842) it should be understood that shield (800) may instead distally terminate at any other suitable location in relation to distal tip (802). For instance, shield (800) may distally terminate at the longitudinal mid-region of blade (842), anywhere proximal to the longitudinal mid-region of blade (842), or anywhere distal to the longitudinal mid-region of blade (842). As another merely illustrative variation, shield (800) may be selectively retractable to selectively expose a distal region of blade (842) or even the full length of blade (842). Various suitable ways in which shield (800) may be selectively retracted and advanced will be apparent to those of ordinary skill in the art in view of the teachings herein.

Figure 17:
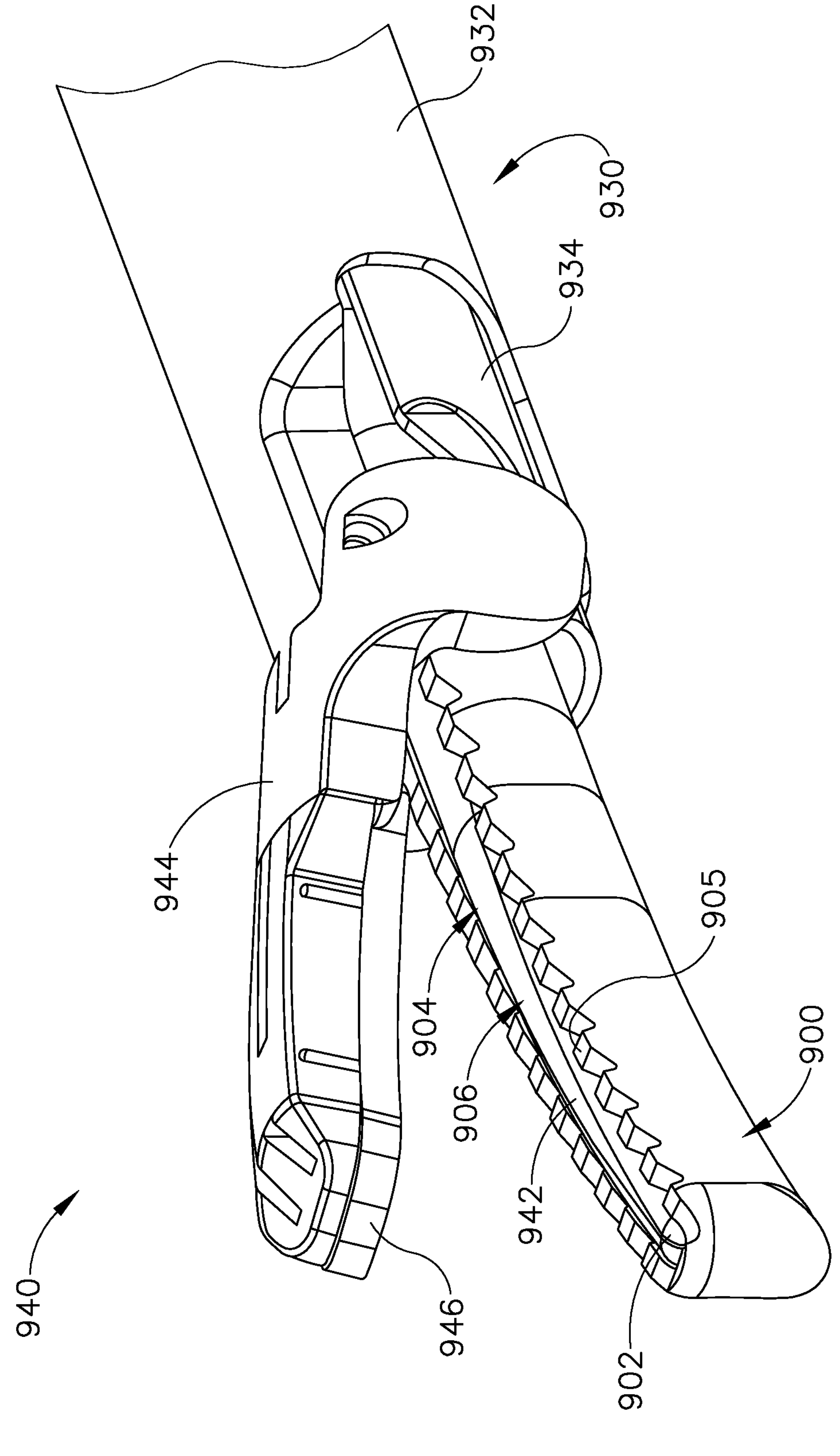
FIG. 17 depicts a perspective view of an end effector with an exemplary alternative ultrasonic blade shield fitted on the ultrasonic blade.

FIG. 17 depicts another exemplary blade shield (900), which is fitted on a blade (942) of an end effector (940). Shield (900) of the present example is formed of a thermally insulative material. By way of example only, shield (900) may comprise silicone, graphine, graphite, and/or any other suitable material(s). End effector (940) of this example is substantially similar to end effector (40) described above. In particular, end effector (940) includes an ultrasonic blade (942) and a pivoting clamp arm (944) with clamp pad (946). Shaft assembly (930) is substantially similar to shaft assembly (30) described above. In particular, shaft assembly (930) includes an outer sheath (932) and an inner tube (934). Clamp arm (944) is pivotally coupled with outer sheath (932) and with inner tube (934), such that clamp arm (944) pivots toward and away from blade (942) in response to translation of inner tube (934) relative to outer sheath (932). Shield (900) may be held in place similar to shield (700) as described above; and/or using any other suitable structures/techniques as will be apparent to those of ordinary skill in the art in view of the teachings herein.

As shown, shield (900) of this example is fitted snugly about blade (942), covering the distal tip (902) of blade (942). However, shield (900) includes an opening (904) that leaves a clamping region (906) of blade (942) exposed. Thus, as clamp arm (944) is pivoted toward blade (942), blade (942) still cuts and seals tissue that is compressed between clamp pad (946) and clamping region (906) of blade (942) just like blade (42) described above. However, shield (900) prevents the rest of blade (942) from coming into direct contact with tissue. Shield (900) may thus prevent blade (942) from inadvertently damaging tissue when blade (942) gets hot during extended use of end effector (940). In some variations, a gap is defined between shield (900) and blade (942). Such a gap may receive vapor and/or fluid from the surgical site. Such vapor and/or fluid may assist in cooling blade (942). While shield (900) of the present example covers distal tip (902) of blade (942) it should be understood that shield (900) may instead distally terminate at any other suitable location in relation to distal tip (902). For instance, shield (900) may distally terminate at the longitudinal mid-region of blade (942), anywhere proximal to the longitudinal mid-region of blade (942), or anywhere distal to the longitudinal mid-region of blade (942). As another merely illustrative variation, shield (900) may be selectively retractable to selectively expose a distal region of blade (942) or even the full length of blade (942). Various suitable ways in which shield (900) may be selectively retracted and advanced will be apparent to those of ordinary skill in the art in view of the teachings herein.

Unlike shield (700) described above, shield (900) of the present example includes a series of teeth (905) adjacent to opening (904). Teeth (905) are configured to assist in gripping of tissue. In the present example, teeth (905) extend past the top plane of clamping region (906) of blade (942), such that teeth (905) will engage tissue clamped between clamp pad (946) and blade (942) before blade (942) engages the tissue. The material forming teeth (905) is soft enough to not pierce or tear the tissue, such that teeth (905) merely provide an enhanced grip on the tissue by end effector (940). Other suitable ways in which a shield may incorporate teeth will be apparent to those of ordinary skill in the art in view of the teachings herein.

Figure 18:
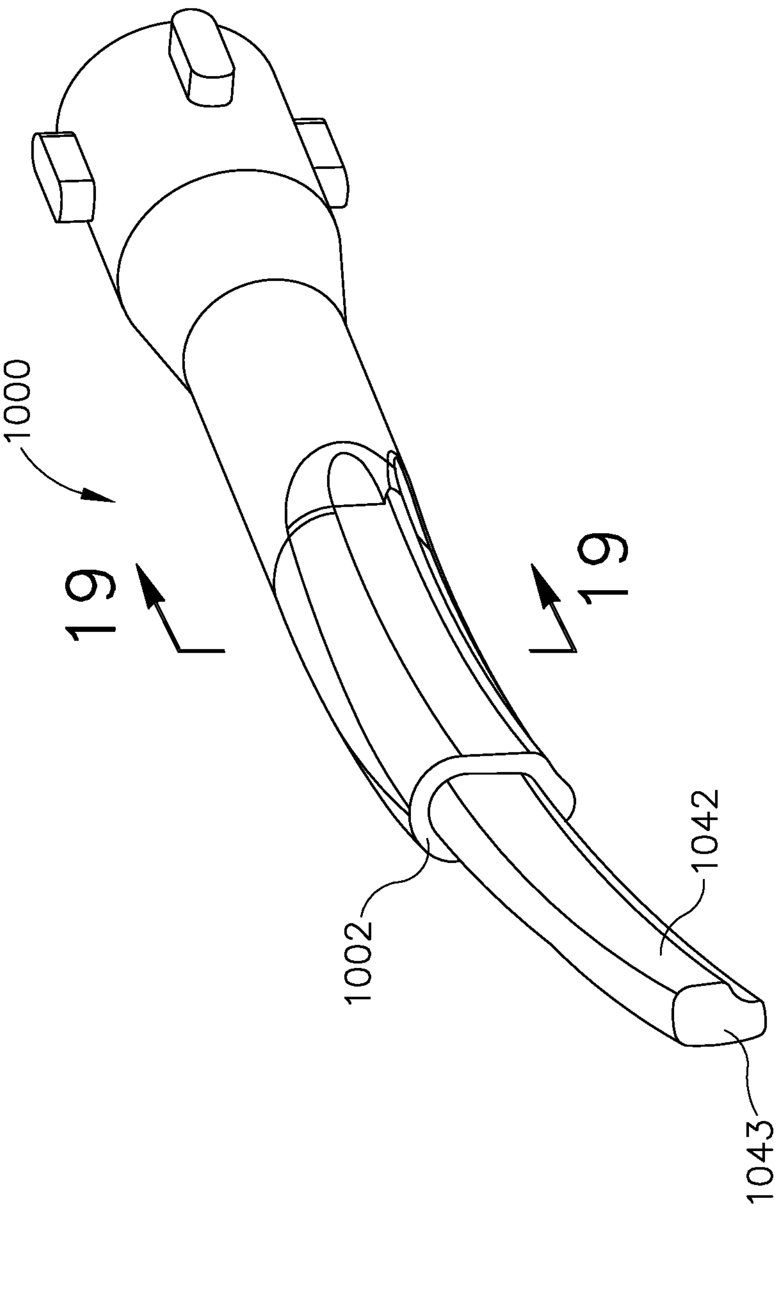
FIG. 18 depicts a perspective view of an ultrasonic blade with another exemplary alternative blade shield.
Figure 19:
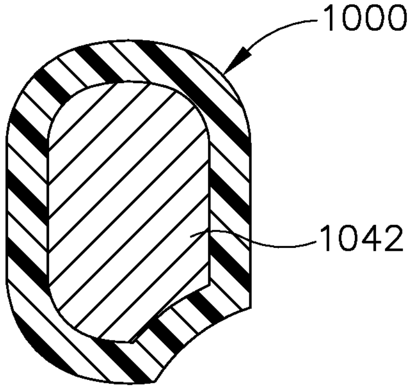
FIG. 19 depicts a cross-sectional end view of the blade and shield of FIG. 18, taken along line 19-19 of FIG. 18.
Figure 20:
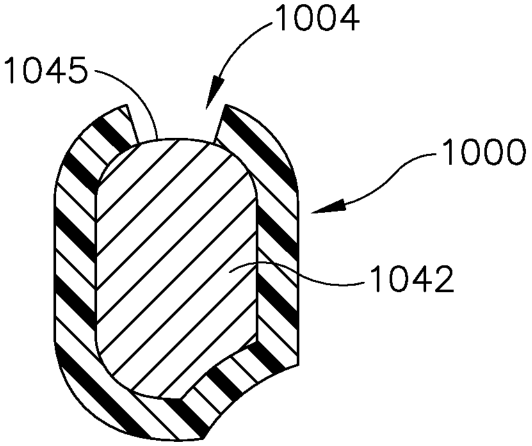
FIG. 20 depicts a cross-sectional end view of the blade and shield of FIG. 18, taken along line 19-19 of FIG. 18, after the shield has been ruptured through use of the end effector.

FIGS. 18-20 show another merely illustrative shield (1000) coupled with an ultrasonic blade (1042). It should be understood that shield (1000) and blade (1042) may be readily incorporated into end effector (40) described above. Shield (1000) of the present example is formed of a thermally insulative material. By way of example only, shield (1000) may comprise silicone, graphine, graphite, and/or any other suitable material(s). Shield (1000) may be held in place similar to shield (700) as described above; and/or using any other suitable structures/techniques as will be apparent to those of ordinary skill in the art in view of the teachings herein.

Unlike shield (700) described above, shield (1000) of this example terminates proximal to the distal tip (1043) of blade (1042). In particular, shield (1000) includes a distal terminal end (1002) that is positioned near the longitudinal mid-region of blade (1042). In some variations, distal terminal end (1002) is positioned somewhere proximal to the longitudinal mid-region of blade (1042); or somewhere distal to the longitudinal mid-region of blade (1042). As another merely illustrative variation, shield (1000) may be selectively retractable to selectively expose a distal region of blade (1042) or even the full length of blade (1042). Various suitable ways in which shield (1000) may be selectively retracted and advanced will be apparent to those of ordinary skill in the art in view of the teachings herein. It should be understood that, by exposing the distal region of blade (1042), shield of the present example use of enables blade (1042) to perform back-cutting operations, spot coagulation, etc. and/or other operations that might not otherwise be possible in versions where the distal region of blade (1042) is covered.

Also unlike shield (700), shield (1000) of the present example extends around the full circumferential perimeter of the profile of blade (1042), as best seen in FIG. 19. In other words, shield (1000) lacks a preformed opening like opening (704). However, after a clamp arm (e.g., similar to clamp arms (44, 744, etc.)) clamps tissue against the combination of blade (1042) and shield (1000) while blade (1042) is ultrasonically activated, the action against shield (1000) may eventually rupture shield as shown in FIG. 20. In particular, such rupturing may define an opening (1004) that is similar to opening (704), exposing a tissue clamping region (1045) of blade (1042). It should be understood that a clamp arm would be clamping toward tissue clamping region (1045) in this example.

Figure 21A:
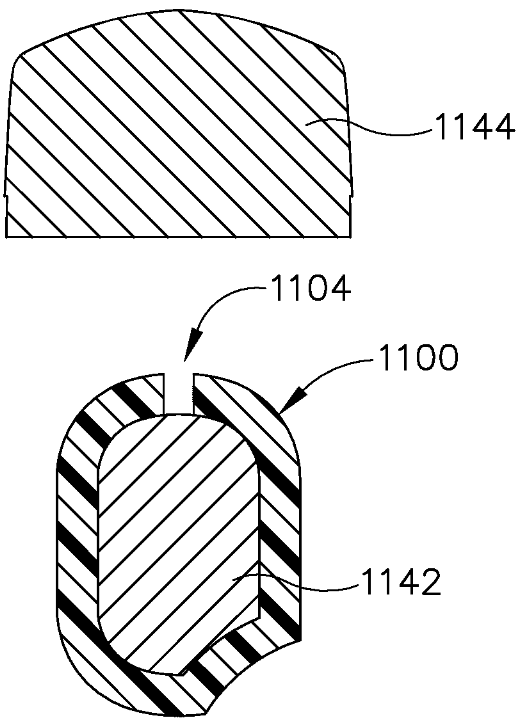
FIG. 21A depicts a cross-sectional end view of an ultrasonic blade with another exemplary alternative blade shield.
Figure 21B:
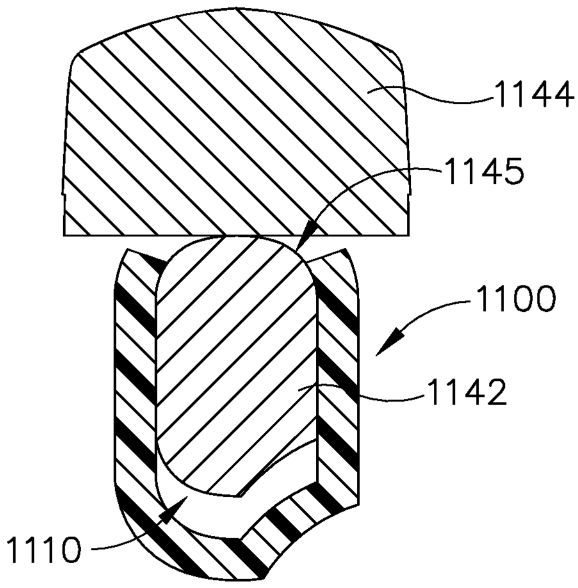
FIG. 21B depicts a cross-sectional end view of the blade and shield of FIG. 21A, with a clamp pad clamping against the blade.

FIGS. 21A-21B depict a merely illustrative variation of shield (1000). In particular FIGS. 21A-21B show a shield (1100) that has a preformed slit (1104). Slit (1104) is positioned adjacent to a tissue clamping region (1145) of a blade (1142). Shield (1100) of the present example is formed of a thermally insulative material. By way of example only, shield (1100) may comprise silicone, graphine, graphite, and/or any other suitable material(s). Shield (1100) of this example may also terminate proximal to the distal tip of blade (1142) (e.g., near the longitudinal mid-region of blade (1142), somewhere proximal to the longitudinal mid-region of blade (1142), or somewhere distal to the longitudinal mid-region of blade (1142)). Shield (1100) may also be selectively retractable relative to blade (1142).

As shown in FIG. 21A, shield (1100) fits closely about blade (1142) when a clamp arm (1144) is positioned away from blade (1142). However, when clamp arm (1144) is pivoted into engagement with blade (1142), shield (1000) deforms at slit (1104) and slides transversely along blade (1142), allowing clamp arm (1144) to contact tissue clamping region (1145) of a blade (1142) as shown in FIG. 21B. In particular, the edges of shield (1100) near slit (1104) spread outwardly to allow shield (1000) to slide transversely relative to blade (1142). During use of blade (1142) and shield (1100), tissue may be interposed between clamp arm (1144) and blade (1142), though it should be understood that shield (1100) may nevertheless still react as shown in FIG. 21B. In the present example, clamp arm (1144) and/or tissue that is interposed between clamp arm (1144) and blade (1142) cause the deformation of shield (1100). In some other versions, one or more features (e.g., camming surfaces, ridges, pegs, etc.) in one or more components such as outer sheath (32) and/or inner tube (34) cause the deformation of shield (1100). Other suitable ways in which shield (1100) may be deformed to expose tissue clamping region (1145) of blade (1142) will be apparent to those of ordinary skill in the art in view of the teachings herein.

As also shown in FIG. 21B, a gap (1110) is defined between the interior of shield (1100) and the exterior of blade (1142) when shield (1100) slides transversely from blade (1142) during deformation of shield (1100) at slit (1104). This gap (1110) may capture vapor plumes emitted during cutting/sealing of tissue by blade (1142) and/or other fluid from a surgical site. Such captured vapor plumes and/or other fluid from a surgical site may assist in cooling of shield (1100) and/or blade (1142). In addition or in the alternative, gap (1110) may provide a path for communicating a cooling fluid (e.g., from a fluid source located proximal to shield (1100) and blade (1142), etc.). Such a cooling fluid may be used to further assist in cooling of shield (1100) and/or blade (1142). In some versions, when clamp arm (1144) is pivoted back away from blade (1142), shield (1100) substantially returns to the configuration shown in FIG. 21A, such that gap (1110) shrinks or substantially disappears. Those of ordinary skill in the art will immediately recognize upon viewing FIGS. 21A-21B that clamp arm (1144) travels along a first plane as clamp arm (1144) moves toward and away from blade (1142); while shield (1100) also travels along the same first plane as shield (1100) moves toward and away from blade (1142). Alternatively, these respective planes of travel may have any other suitable relationship. It should also be understood upon viewing FIGS. 21A-21B that movement of clamp arm (1144) drives the movement of shield (1100) in this example. Other suitable ways in which movement of a clamp arm may drive movement of a shield will be apparent to those of ordinary skill in the art in view of the teachings herein.

Figure 22:
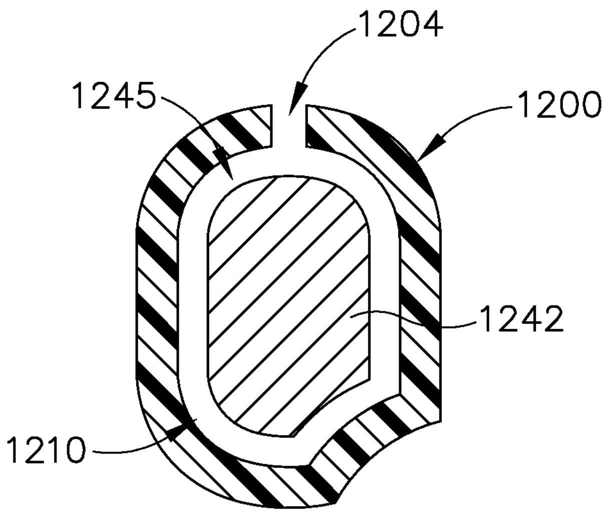
FIG. 22 depicts a cross-sectional end view of an ultrasonic blade with another exemplary alternative blade shield.
Figure 23:
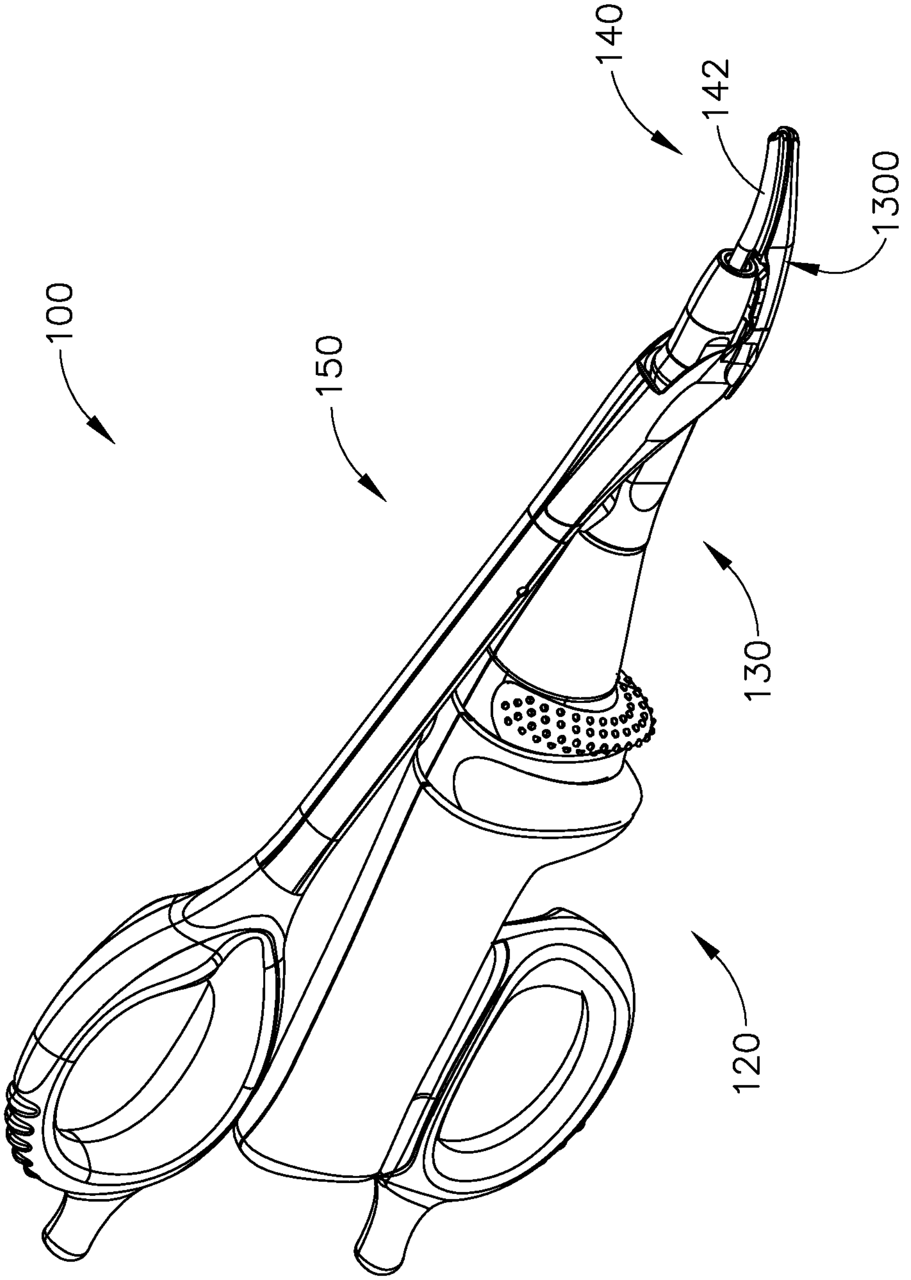
FIG. 23 depicts a perspective view of the instrument of FIG. 4 with an exemplary clamp arm shield secured to the clamp arm.
Figure 24:
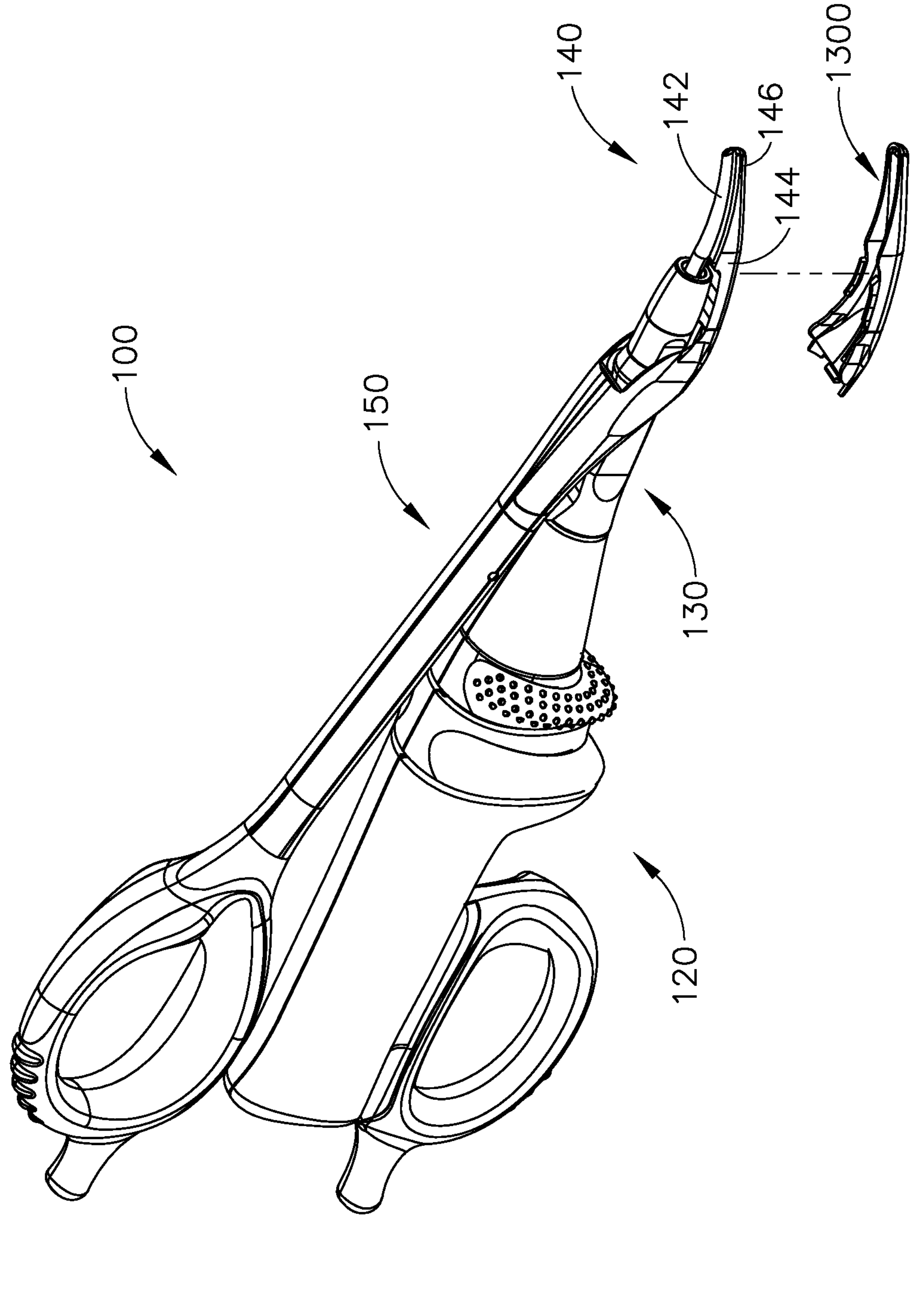
FIG. 24 depicts a perspective view of the instrument of FIG. 4 with the clamp arm shield of FIG. 23 separated from the clamp arm.
Figure 25:
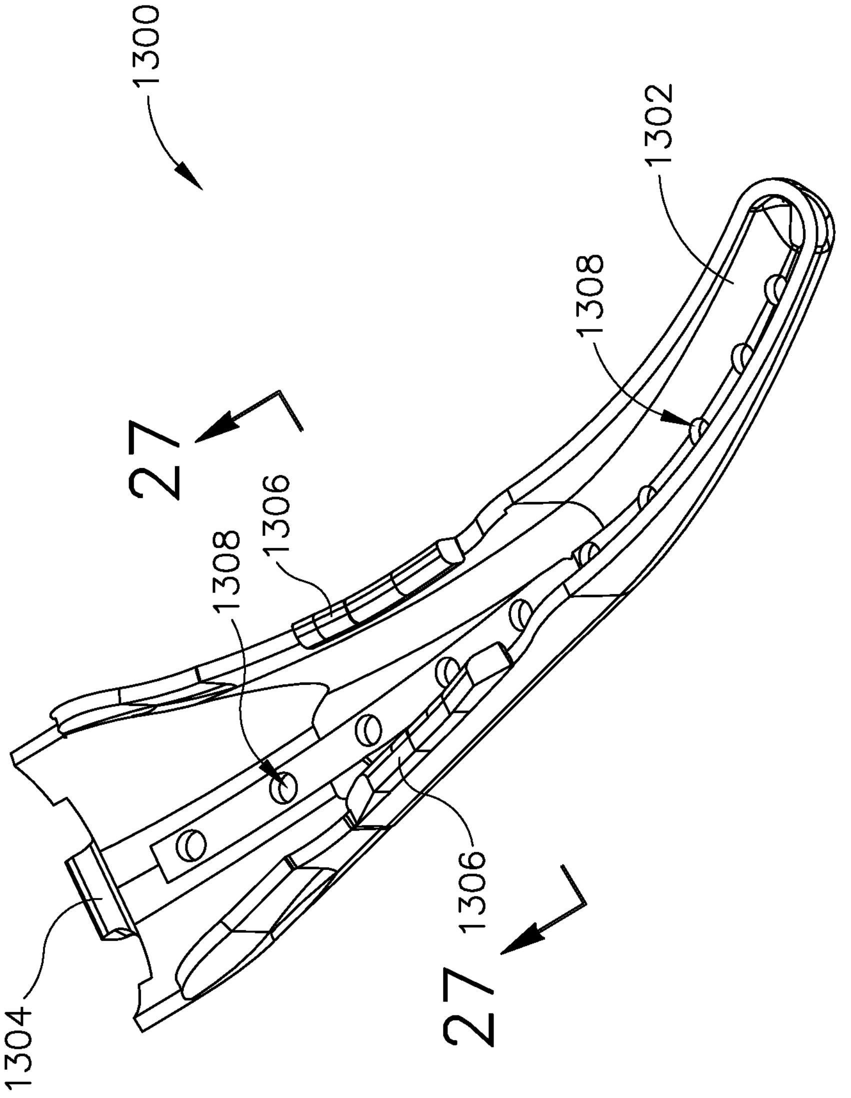
FIG. 25 depicts a perspective view of the shield of FIG. 23.
Figure 26:
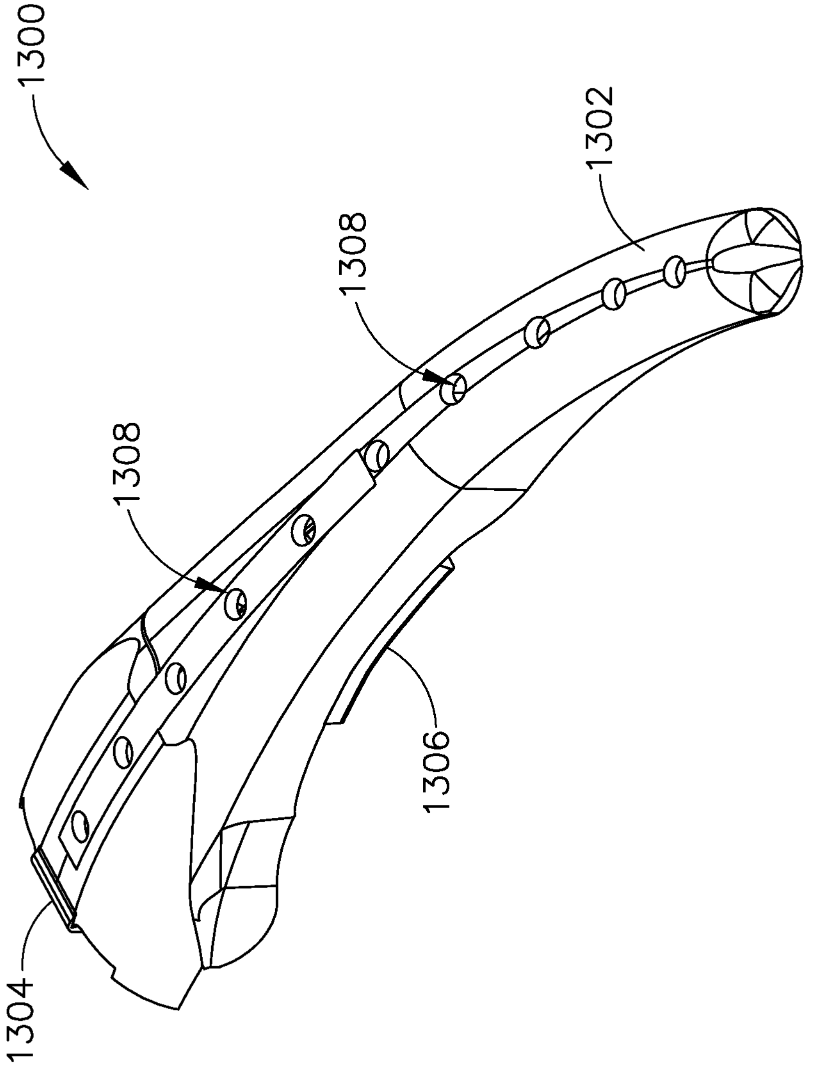
FIG. 26 depicts another perspective view of the shield of FIG. 23.
Figure 27:
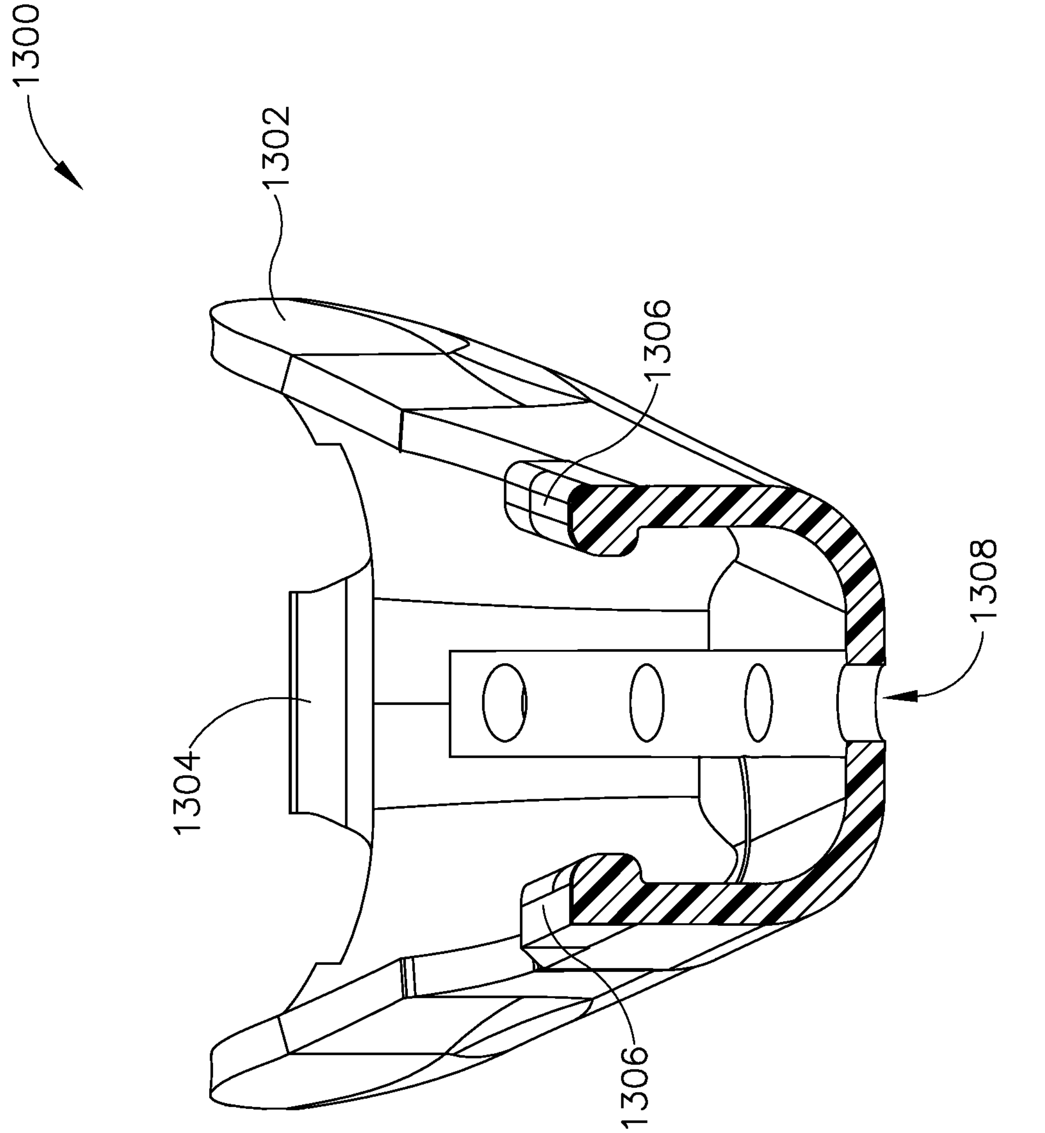
FIG. 27 depicts a cross-sectional view of the shield of FIG. 23, taken along line 27-27 of FIG. 25.
Figure 28:
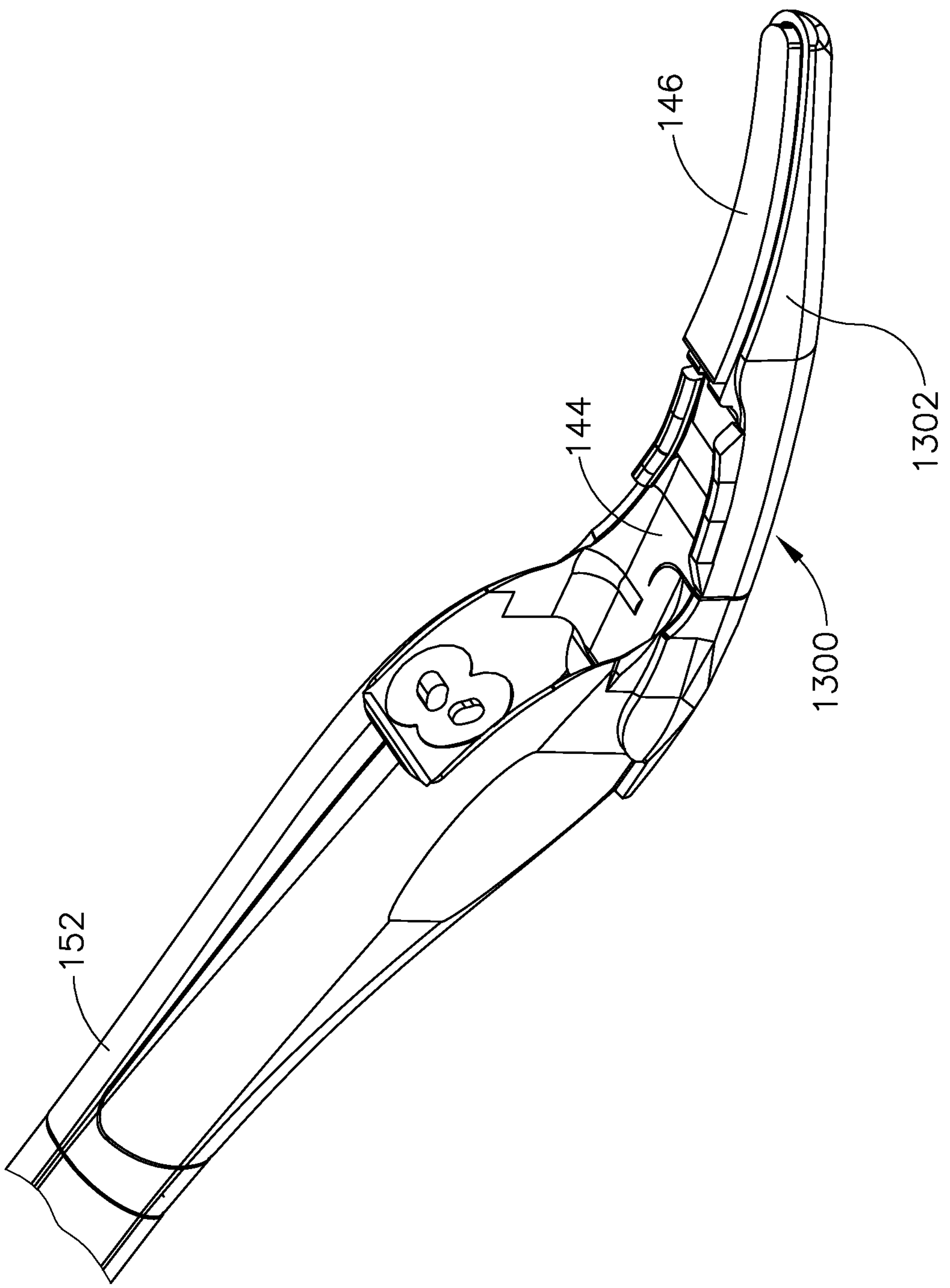
FIG. 28 depicts a perspective view of the clamp arm of the instrument of FIG. 4 with the shield of FIG. 23 secured thereto.
Figure 29:
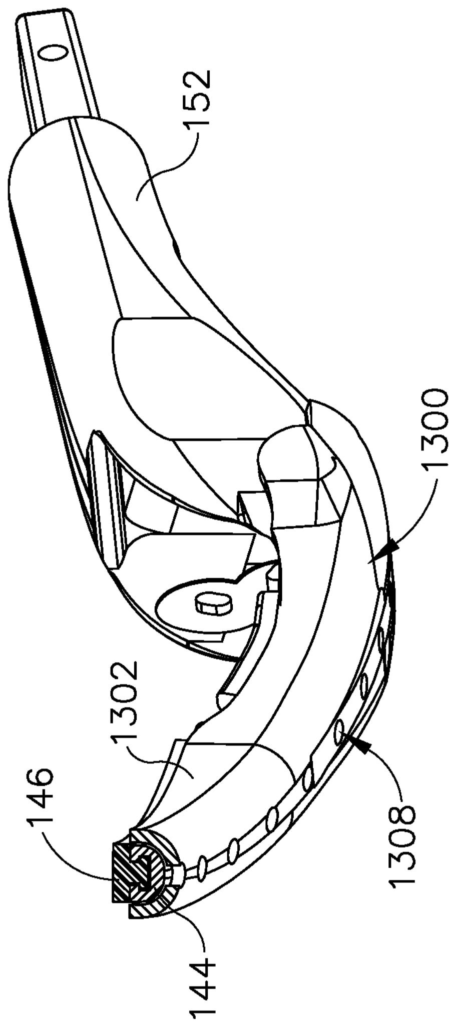
FIG. 29 depicts a cross-sectional view of the clamp arm of the instrument of FIG. 4 with the shield of FIG. 23 secured thereto.

FIG. 22 shows a merely illustrative variation of shield (1100). In particular FIG. 22 shows a shield (1200) that has a preformed slit (1204) positioned adjacent to a tissue clamping region (1245) of a blade (1242). Shield (1200) of the present example is formed of a thermally insulative material. By way of example only, shield (1200) may comprise silicone, graphine, graphite, and/or any other suitable material(s). Shield (1200) of this example may also terminate proximal to the distal tip of blade (1242) (e.g., near the longitudinal mid-region of blade (1242), somewhere proximal to the longitudinal mid-region of blade (1242), or somewhere distal to the longitudinal mid-region of blade (1242)). Shield (1200) may also be selectively retractable relative to blade (1242). Unlike shield (1100), shield (1200) of this example does not fit closely about blade (1242) when a clamp arm is positioned away from blade (1242). Instead, shield (1200) of this example defines a gap (1210) between the interior of shield (1200) and the exterior of blade (1242), even when a clamp arm is spaced away from shield (1200) and blade (1242). This may further promote capture of vapor/fluid and/or communication of a cooling fluid, to assist in cooling blade (1242) and/or shield (1200), etc. Shield (1200) of this example may still deform and slide transversely relative to blade (1242) in a manner similar to shield (1100) as shown in FIG. 21B.

Still other suitable features, configurations, and operabilities for shields that may be fitted on an ultrasonic blade such as blades (42, 142) will be apparent to those of ordinary skill in the art in view of the teachings herein.

D. Exemplary Clamp Arm Shield

In addition to or as an alternative to providing a shield for an ultrasonic blade such as blades (42, 142), a shield may be provided for a clamp arm such as clamp arms (44, 144). By way of example only, FIGS. 23-30 show a shield (1300) that is selectively coupled with clamp arm (144) of instrument (100). Shield (1300) of this example comprises a body (1302) with a proximal engagement feature (1304), a pair of lips (1306), and a series of openings (1308) spaced along the length of body (1302). In the present example, body (1302) is formed of a rigid plastic material that is thermally insulative. Other suitable materials (e.g., ceramic, rubber, metal with a thermally insulative coating, etc.) that may be used to form body (1302) will be apparent to those of ordinary skill in the art in view of the teachings herein.

Engagement feature (1304) is configured to engage a portion of clamp arm (144) to thereby assist with seating of shield (1300) on clamp arm (144). Lips (1306) extend laterally and inwardly toward each other. Lips (1306) are configured to provide a snap fit on clamp arm (144). In other words, in order to secure shield (1300) to clamp arm (144), the operator may first seat engagement feature (1304) at the proximal portion of clamp arm (144), then pivot the distal end of shield (1300) toward the distal end of clamp arm (144). During this movement, lips (1306) may deflect outwardly until they clear an upper surface of clamp arm (144), at which point they snap into place over the outer regions of the upper surface of clamp arm (144). This snap fitting may allow shield (1300) to be replaced as needed. Of course, shield (1300) may be removably or permanently secured to clamp arm (144) in any other suitable fashion. It should also be understood that shield (1300) may be an integral feature of clamp arm (144).

In the present example, body (1302) is configured to complement the curved profile of clamp arm (144). Nevertheless, body (1302) is also configured to provide a gap between the outer surface of clamp arm (144) and the inner surface of body (1302). Openings (1308) are in fluid communication with this gap. These openings (1308) thus allow the flow of air and liquids into and out of the gap defined between clamp arm (144) and body (1302). It should therefore be understood that the gap and openings (1308) cooperate to provide cooling of the material forming clamp arm (144) by way of convection; while also serving as a break to inhibit conduction of heat from clamp arm (144) to body (1302) of shield (1300). In some versions, clamp arm (144) is formed of a metallic material (e.g., aluminum, etc.), such that clamp arm (144) cools by convection relatively easily.

In view of the foregoing, since shield (1300) provides a convection cooling path and prevents tissue from contacting clamp arm (144) directly, shield (1300) may provide protection against damage to tissue through inadvertent contact with a hot clamp arm (144). It should be understood that clamp pad (146) remains exposed relative to shield (1300), such that shield (1300) does not impede the ability of end effector (140) to clamp, cut, and seal tissue. It should also be understood that shield (1300) has a low profile such that shield (1300) does not impede the ability of end effector (140) to perform blunt dissections (e.g., by positioning a closed end effector (140) between layers of tissue and then opening end effector (140) to separate those layers of tissue, etc.). Other suitable features, configurations, and properties for shield (1300) will be apparent to those of ordinary skill in the art in view of the teachings herein.

Figure 30:
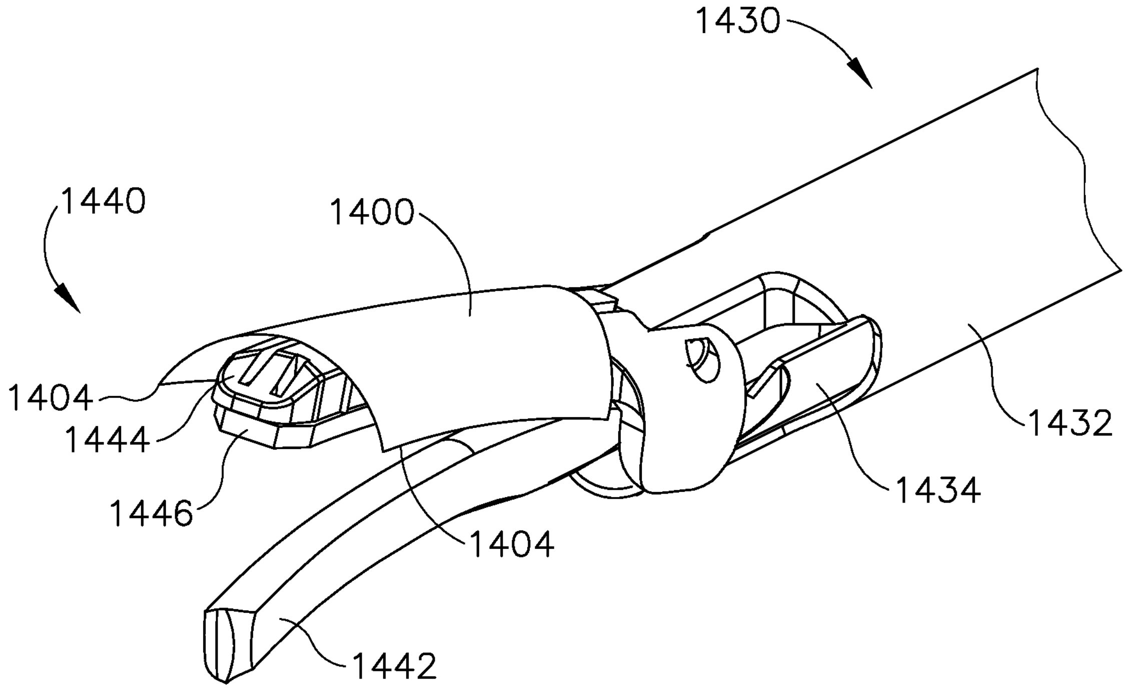
FIG. 30 depicts a perspective view of another exemplary alternative end effector, with a clamp arm shield secured to the clamp arm.
Figure 31:
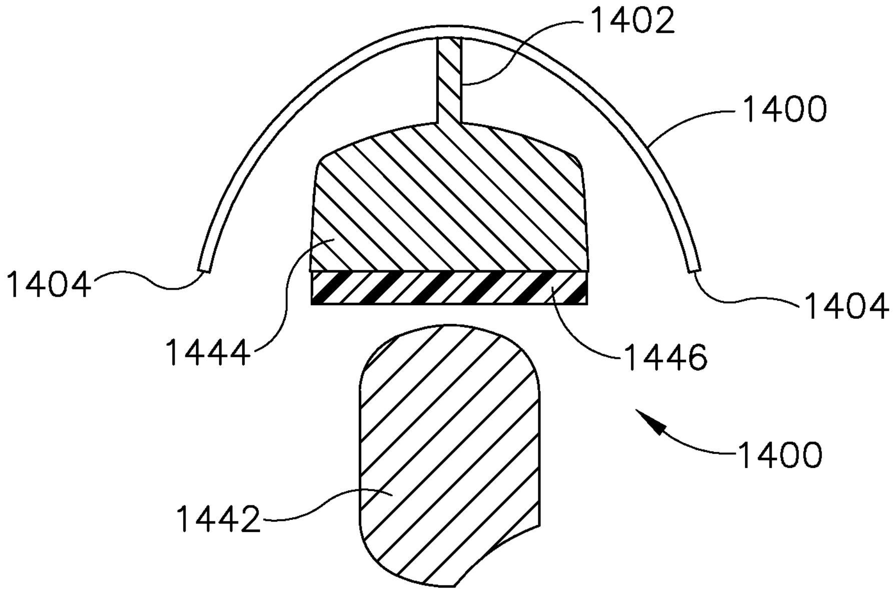
FIG. 31 depicts a cross-sectional end view of the end effector and clamp arm shield of FIG. 30.
Figure 32:
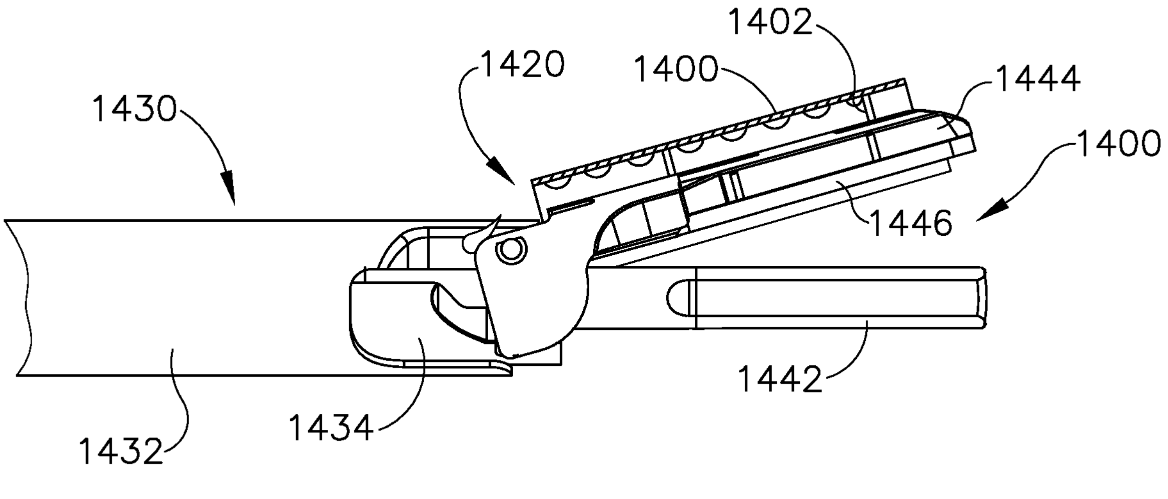
FIG. 32 depicts a side elevational view of the end effector and clamp arm shield of FIG. 30, with the clamp arm shield shown in cross-section.

FIGS. 30-32 show an exemplary alternative end effector (1440) with a shield (1400). End effector (1440) of this example is substantially similar to end effector (40) described above. In particular, end effector (1440) includes an ultrasonic blade (1442) and a pivoting clamp arm (1444) with clamp pad (1446). Shaft assembly (1430) is substantially similar to shaft assembly (30) described above. In particular, shaft assembly (1430) includes an outer sheath (1432) and an inner tube (1434). Clamp arm (1444) is pivotally coupled with outer sheath (1432) and with inner tube (1434), such that clamp arm (1444) pivots toward and away from blade (1442) in response to translation of inner tube (1434) relative to outer sheath (1432).

Shield (1400) of the present example is secured to clamp arm (1444) by a plurality of struts (1402). By way of example only, struts (1402) may be formed as integral extensions that snap into clamp arm (1444). Other suitable ways in which struts (1402) may be configured and coupled with clamp arm (1444) will be apparent to those of ordinary skill in the art in view of the teachings herein. Struts (1402) define a gap between the outer surface of clamp arm (1444) and the inner surface of shield (1400). The outer lateral edges (1404) of shield (1400) are also spaced away from clamp arm (1444), such that the gap is open along the length of shield (1400) on both sides of shield. It should therefore be understood that the gap provides cooling of the material forming clamp arm (1444) by way of convection; while also serving as a break to inhibit conduction of heat from clamp arm (1444) to shield (1400). In some versions, clamp arm (1444) is formed of a metallic material (e.g., aluminum, etc.), such that clamp arm (1444) cools by convection relatively easily.

In view of the foregoing, since shield (1400) provides a convection cooling path and prevents tissue from contacting clamp arm (1444) directly, shield (1400) may provide protection against damage to tissue through inadvertent contact with a hot clamp arm (1444). In addition, shield (1400) may provide a substrate for condensation from steam/vapor emitted during use of end effector (1440) on tissue. In particular, the steam/vapor may enter the gap between clamp arm (1444) and shield (1400), with condensate (1420) forming on the inner surface of shield (1400). The gathered steam/vapor may assist in cooling clamp arm (1444). In addition, at least some of the condensate (1420) that forms on the inner surface of shield (1400) may drip from shield (1400) onto clamp arm (1444), providing further cooling of clamp arm (1444). In some instances, when clamp arm (1444) is pivoted away from blade (1442), the condensate (1420) may run proximally along the inner surface of shield (1400) and eventually drip onto blade (1442) as shown in FIG. 32, thereby providing cooling for blade (1442). Shield (1400) may thus provide cooling of clamp arm (1444), provide cooling of blade (1442), and prevent direct contact between tissue and the outer surface of clamp arm (1444).

In the present example, shield (1400) is formed of a resilient plastic material that is thermally insulative. This resilience may enable outer lateral edges (1404) of shield (1400) to deflect inwardly, to thereby reduce the effective width of shield (1400), as end effector (1440) and shield (1400) are inserted through a trocar. Once end effector (1440) and shield (1400) exit the trocar, the resilience of shield (1400) may cause outer lateral edges (1404) to spring back outwardly to the positions shown in FIGS. 30-31. Other suitable materials that may be used to form shield (1400) will be apparent to those of ordinary skill in the art in view of the teachings herein.

Figure 33:
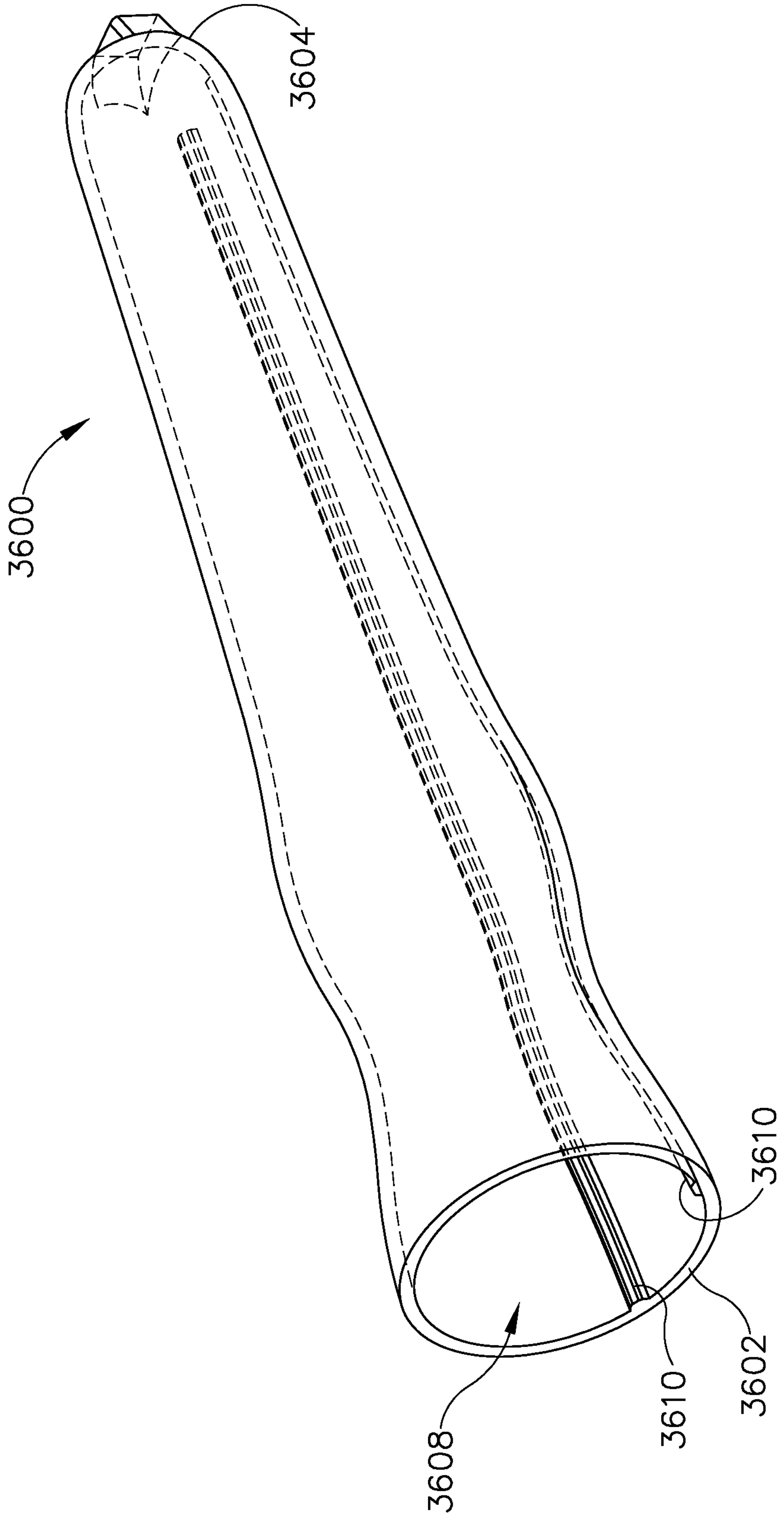
FIG. 33 depicts a perspective view of an exemplary clamp arm sleeve.
Figure 34A:
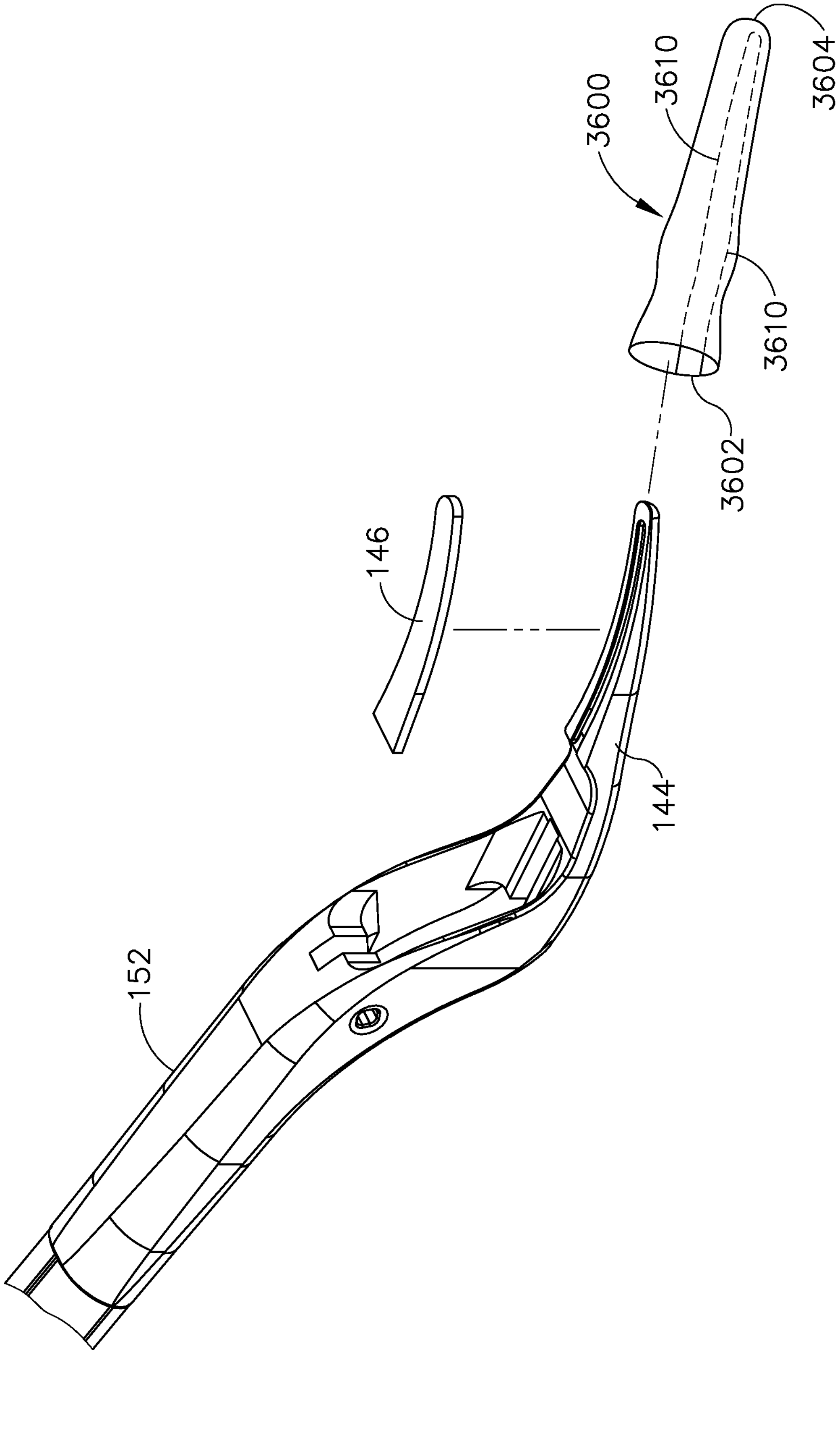
FIG. 34A depicts an exploded perspective view of an exemplary assembly including the clamp arm sleeve of FIG. 33 separated from the clamp arm of the end effector of FIG. 5.
Figure 34B:
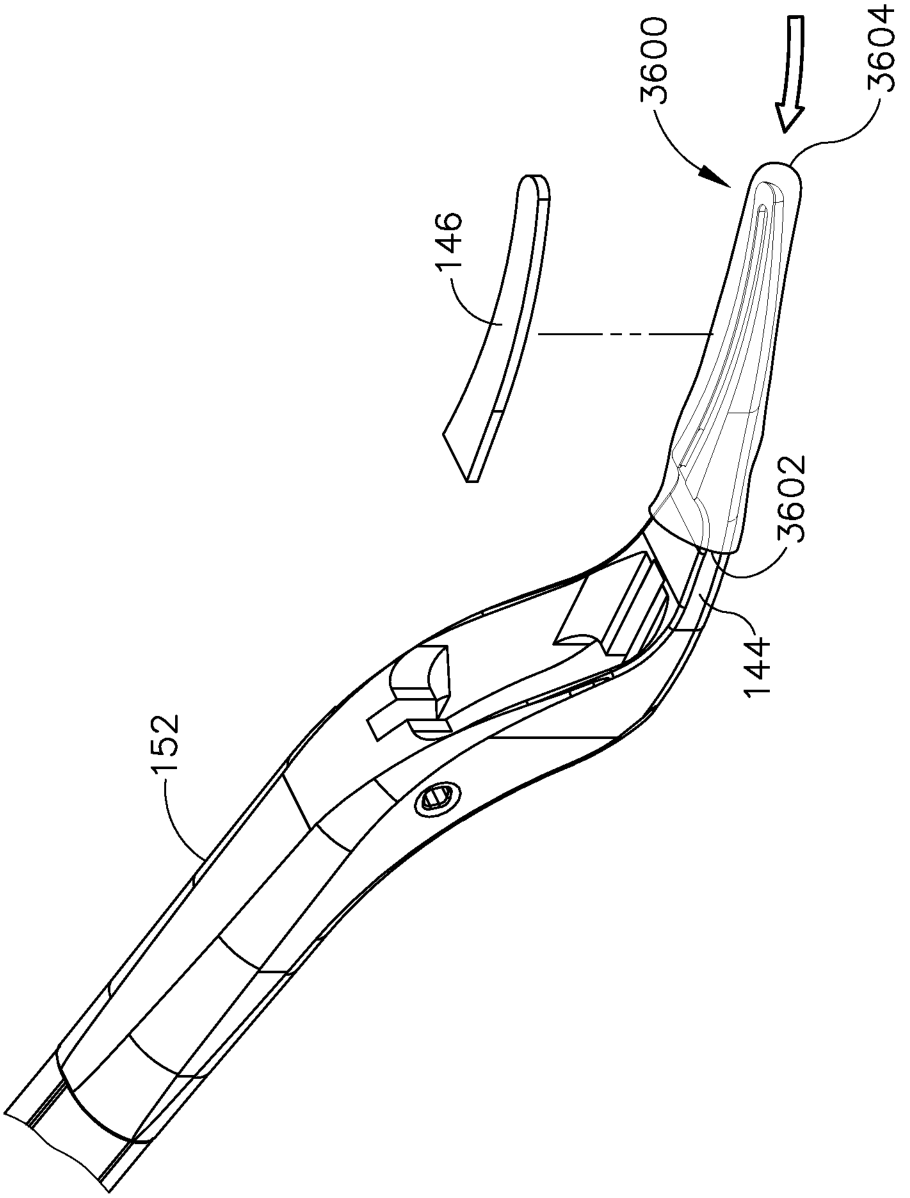
FIG. 34B depicts an exploded perspective view of the assembly of FIG. 34A including the clamp arm sleeve of FIG. 33 joined to the clamp arm of the end effector of FIG. 5.
Figure 34C:
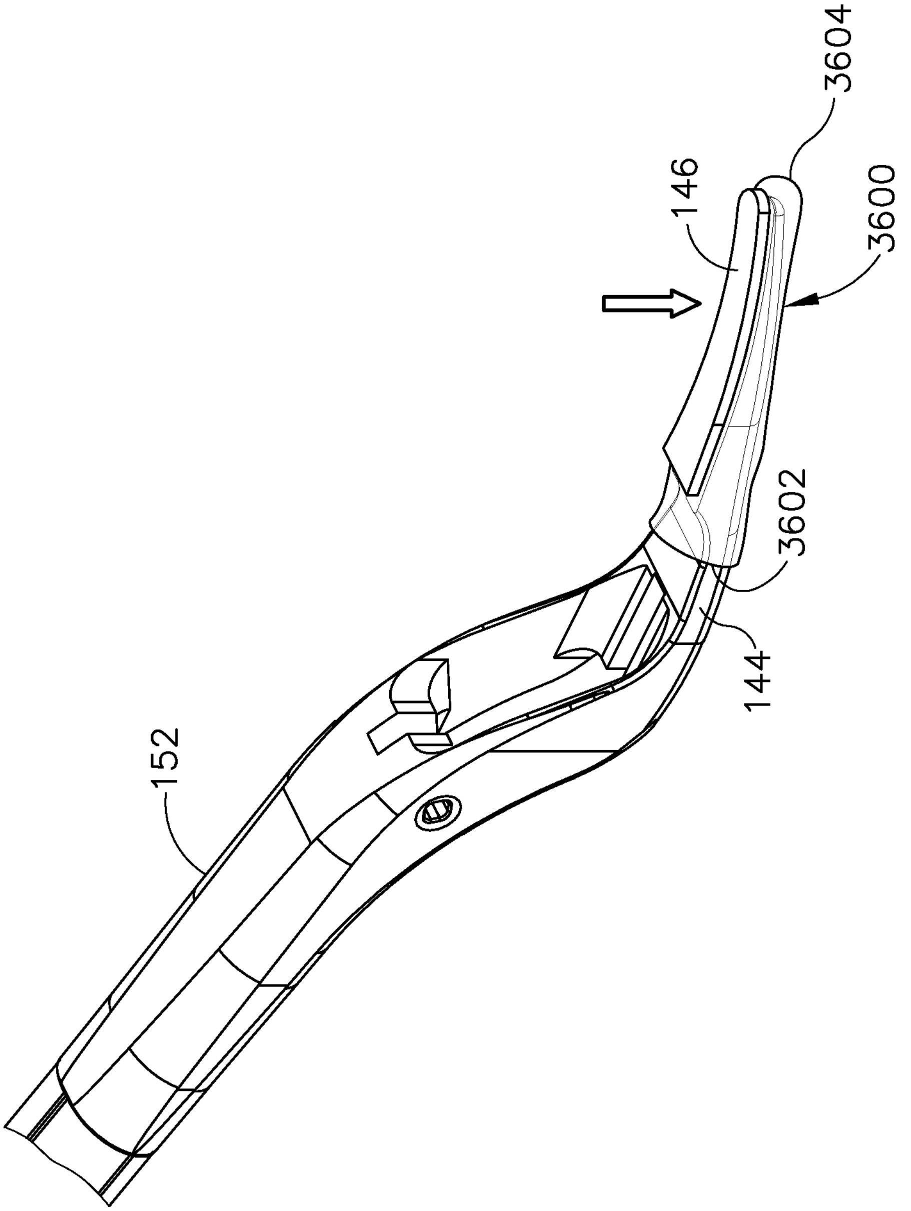
FIG. 34C depicts a perspective view of the assembly of FIG. 34A including the clamp arm sleeve of FIG. 33 joined to the clamp arm of the end effector of FIG. 5, with the clamp pad further joined to the clamp arm.
Figure 35:
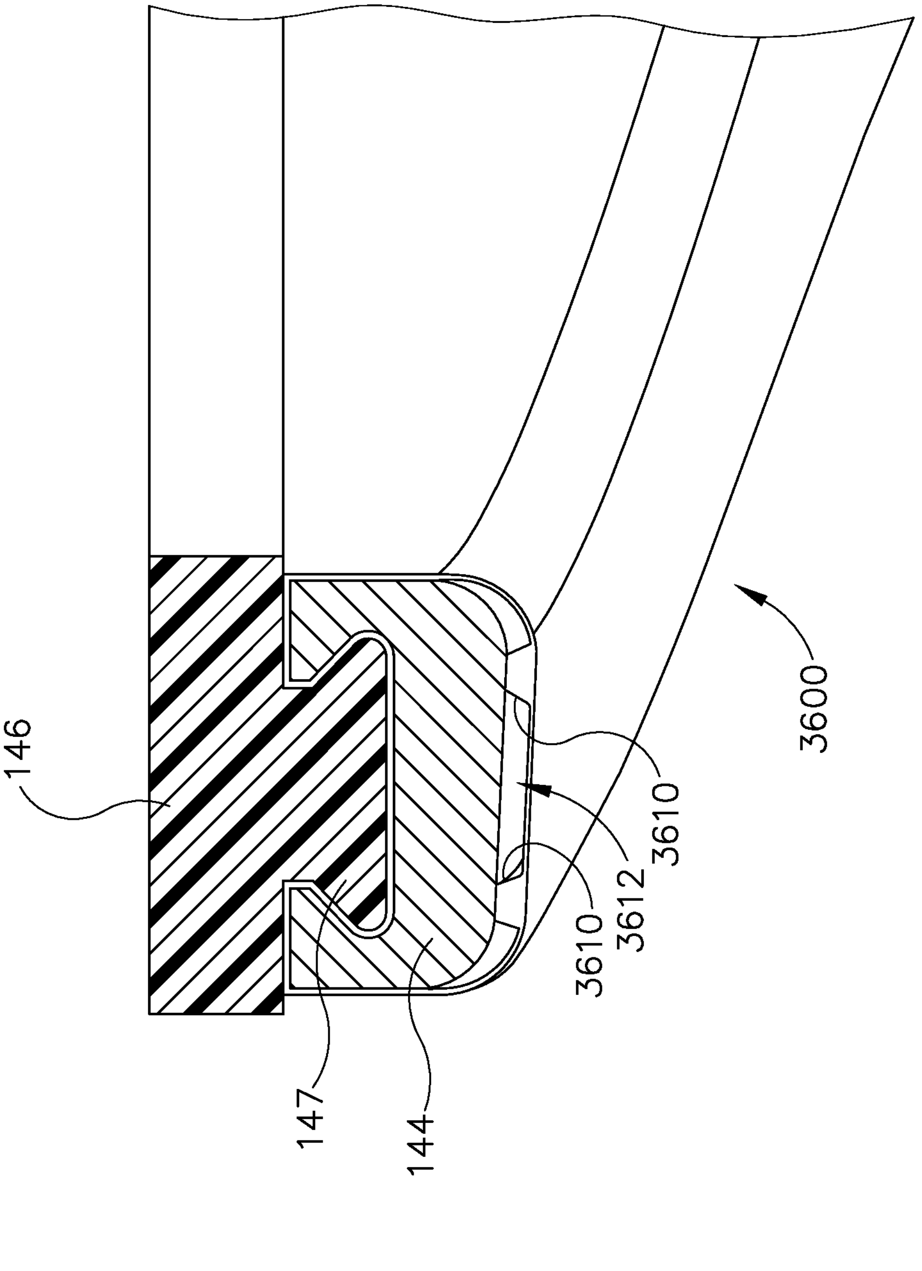
FIG. 35 depicts a cross-sectional end view of the assembly of FIG. 34A.

FIGS. 33-35 show another exemplary sleeve (3600) that may be readily secured to clamp arm (144) of instrument (100). Sleeve (3600) of this example includes an open proximal end (3602) and a closed distal end (3604), such that sleeve (3600) defines a hollow interior (3608). A pair of stand-off ribs (3610) extend longitudinally through interior (3608), from open proximal end (3602) to closed distal end (3604). Sleeve (3600) is configured to fit between clamp pad (146) and clamp arm (144). In particular, as shown in the transition from FIG. 34A to FIG. 34B, the distal end of clamp arm (144) may be inserted into open proximal end (3602) of sleeve (3600), such that sleeve (3600) may be slid onto clamp arm (144), before clamp pad (146) is secured to clamp arm (144). As shown in the transition from FIG. 34B to FIG. 34C, clamp pad (146) is then secured to clamp arm (144), such that a portion of sleeve (3600) is interposed between clamp pad (146) and clamp arm (144). In particular, and as best seen in FIG. 35, a portion of sleeve (3600) is captured between a securing rail (147) of clamp pad (146) and a complementary recess of clamp arm (144). In the present example, sleeve (3600) is not removable from clamp arm (144) after sleeve (3600) has been assembled with clamp arm (144) and clamp pad (146).

As also seen in FIG. 35, standoff ribs (3610) are configured to define a gap (3612) within hollow interior (3602), between clamp arm (144) and sleeve (3600). This gap (3612) may create a thermal barrier, substantially preventing conductive heat transfer from clamp arm (144) to sleeve (3600). In some versions, sleeve (3600) further includes openings in fluid communication with gap (3612), which may provide cooling of the material forming clamp arm (144) by way of convection; while also allowing fluids to reach clamp arm (144). In the present example, standoff ribs (3610) are simply formed by regions of the sidewall of sleeve (3600) that have a greater thickness than other regions of sleeve (3600). By way of example only, sleeve (3600) may be formed of silicone rubber. Other suitable materials that may be used to form sleeve (3600) will be apparent to those of ordinary skill in the art in view of the teachings herein.

In view of the foregoing, since sleeve (3600) provides a convection cooling path and/or prevents tissue from contacting clamp arm (144) directly, sleeve (3600) may provide protection against damage to tissue through inadvertent contact with a hot clamp arm (144). It should be understood that clamp pad (146) remains exposed relative to sleeve (3600), such that sleeve (3600) does not impede the ability of end effector (140) to clamp, cut, and seal tissue. It should also be understood that sleeve (3600) has a low profile such that sleeve (3600) does not impede the ability of end effector (140) to perform blunt dissections (e.g., by positioning a closed end effector (140) between layers of tissue and then opening end effector (140) to separate those layers of tissue, etc.). In some instances, clamp arm (144) has additional structural features (e.g., a distal tissue dissection protrusion, etc.). Sleeve (3600) may readily conform to such features and/or be made to conform to such features. Other suitable features, configurations, and properties for sleeve (3600) will be apparent to those of ordinary skill in the art in view of the teachings herein.

Any of the shields/sleeves described above may include a visual marking indicating where the distal end of the ultrasonic blade meets the clamp pad. This may facilitate positioning of the end effector when the blade is obscured from the operator's view. In addition or in the alternative, the distal end of any of the shields/sleeves described above may include a blunt or sharp outwardly extending protrusion (e.g., similar to an egg tooth) that promotes gripping of tissue during blunt dissection operations. Still other suitable features, configurations, and operabilities for shields that may be fitted on a clamp arm such as clamp arms (44, 144) will be apparent to those of ordinary skill in the art in view of the teachings herein.

E. Exemplary Blade Capture Features

Figure 36A:
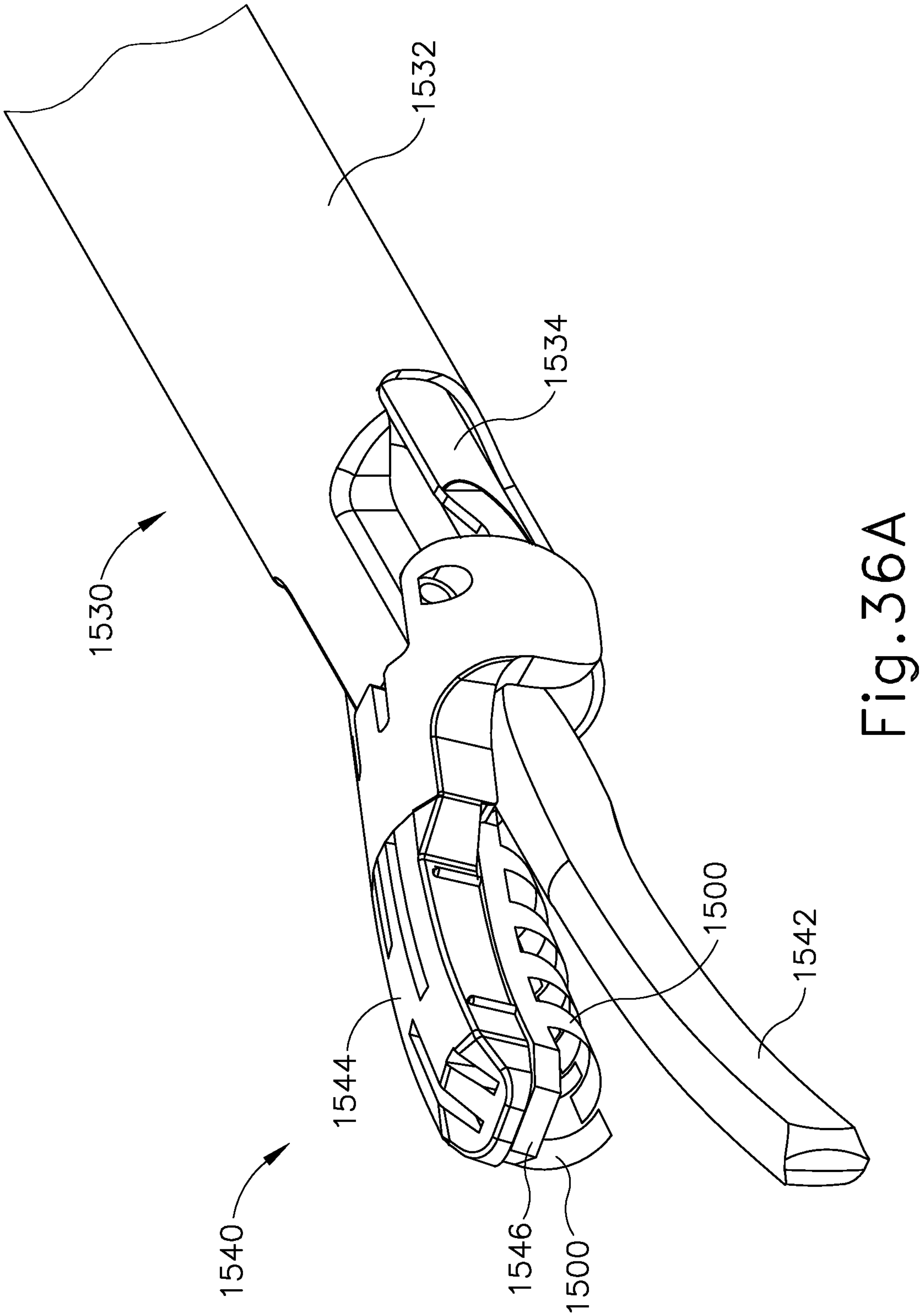
FIG. 36A depicts a perspective view of another exemplary alternative end effector, in an open configuration.
Figure 36B:
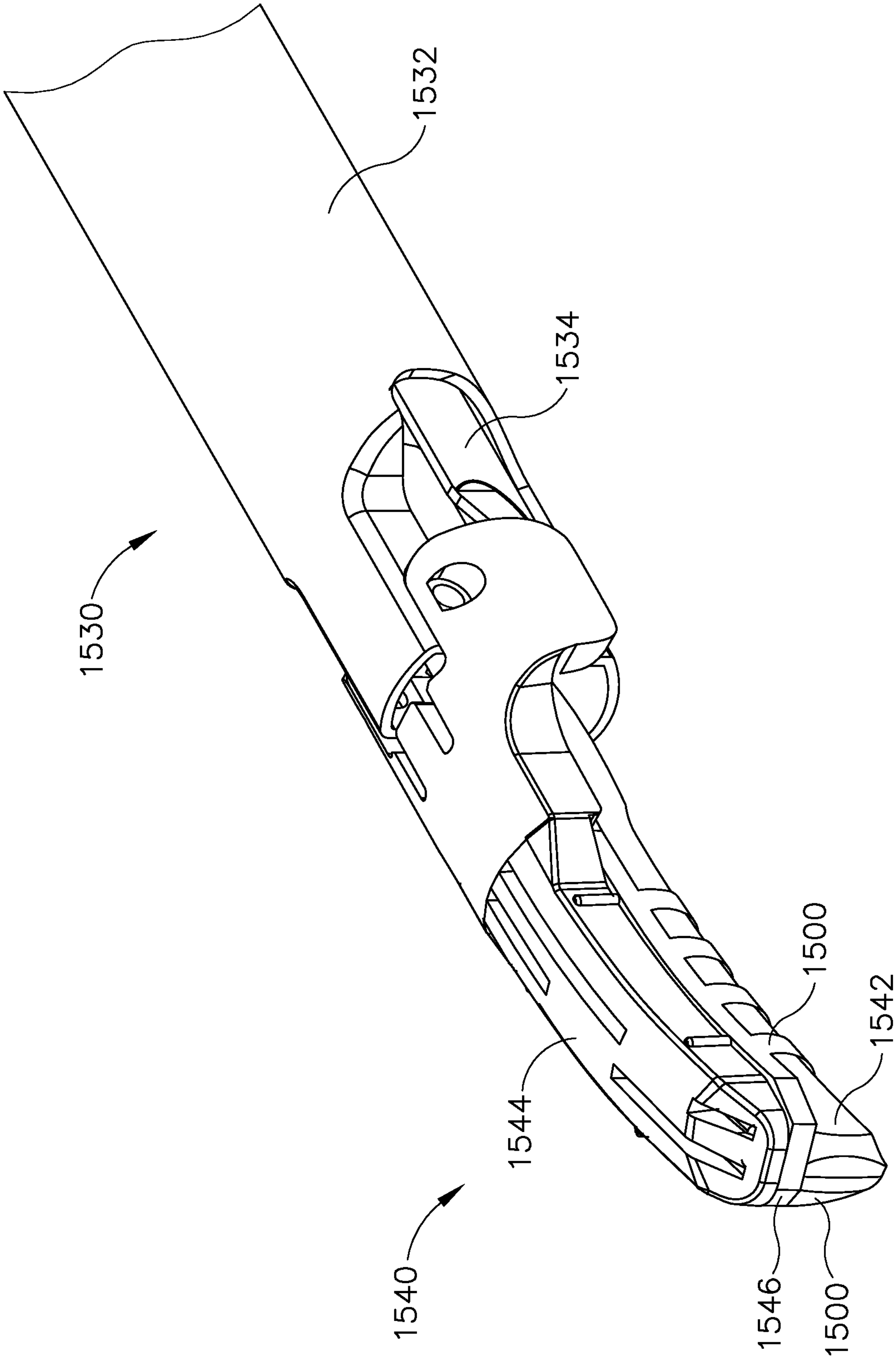
FIG. 36B depicts a perspective view of the end effector of FIG. 36A, in a closed configuration.
Figure 37:
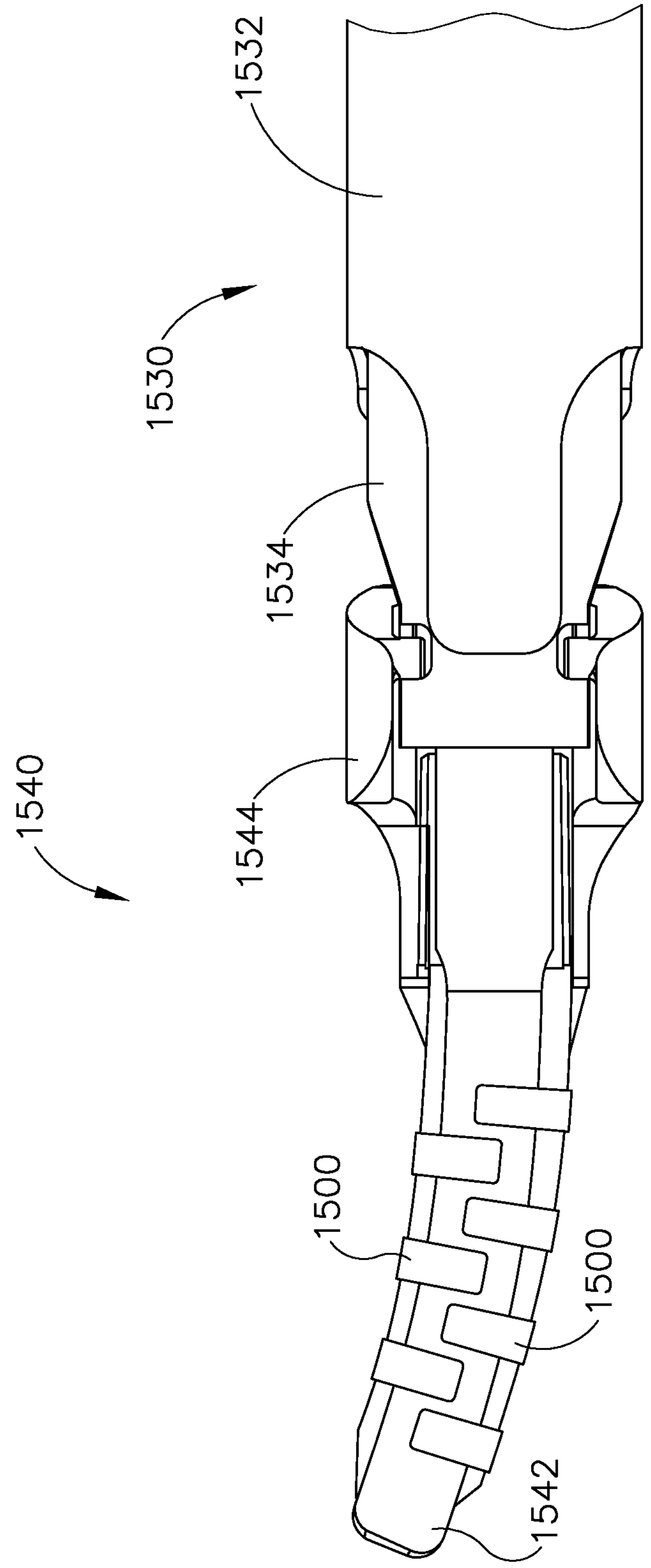
FIG. 37 depicts a bottom plan view of the end effector of FIG. 36A, in the closed configuration.

FIGS. 36A-37 show an exemplary alternative end effector (1540). End effector (1540) of this example is substantially similar to end effector (40) described above. In particular, end effector (1540) includes an ultrasonic blade (1542) and a pivoting clamp arm (1544) with clamp pad (1546). Shaft assembly (1530) is substantially similar to shaft assembly (30) described above. In particular, shaft assembly (1530) includes an outer sheath (1532) and an inner tube (1534). Clamp arm (1544) is pivotally coupled with outer sheath (1532) and with inner tube (1534), such that clamp arm (1544) pivots toward and away from blade (1542) in response to translation of inner tube (1534) relative to outer sheath (1532).

Clamp pad (1546) of the present example comprises a plurality of arcuate fingers (1500). Fingers (1500) of this example extend generally transversely and are arranged in an alternating pattern along the length of clamp pad, such that fingers (1500) are interdigitated. Fingers (1500) are formed of a resilient material (e.g., plastic, etc.), such that fingers (1500) deflect outwardly and then substantially close about blade (1542) as clamp arm (1544) is pivoted toward blade (1542). It should be understood that the spaces between fingers (1500) may provide wicking channels for fluids at a surgical site. In either case, wicking may be provided through a capillary action while blade (1542) and fingers (1500) are engaging tissue. Once the tissue is released from blade (1542) and clamp arm (1544), the wicked fluid may assist in cooling blade (1542) and/or clamp arm (1544) through conduction and phase change.

In addition or in the alternative, wicking channels may be formed in the inner surfaces of fingers (1500). In one merely illustrative variation, fingers (1500) are substituted with continuous hoops that each extend from one lateral side of clamp pad (1546) to the other lateral side of clamp pad (1546). Such hoops may also have spaces therebetween that provide wicking channels for fluids at a surgical site, which may assist in cooling blade (1542) and/or clamp arm (1544) as described above. In addition or in the alternative, wicking channels may be formed in the inner surfaces of the hoops. Regardless of whether fingers (1500), hoops, or some other structural features are used, the fingers (1500), hoops, or other structural features may be coated with a hydrophilic material (e.g., HYDAK® T-070 or HYDAK® T-018 by Biocoat Incorporated of Horsham, Pennsylvania) to assist in fluid retention for cooling purposes. It should also be understood that the fingers (1500), hoops, or other structural features may serve as shields, preventing inadvertent contact between a hot blade (1542) and tissue and/or a hot clamp arm (1544) and tissue. Other suitable configurations and properties for clamp pad (1546) will be apparent to those of ordinary skill in the art in view of the teachings herein.

III. Miscellaneous

In addition to or as an alternative to using shielding to reduce heat in a version of instrument (10, 100), a fluid may be used to cool blade (42, 142). For instance, a cooling liquid (e.g., saline, etc.) may be applied to the proximal end of blade (42, 142). The cooling fluid may then be communicated distally along the rest of the length of blade (42, 142) to thereby cool blade. The ultrasonic vibration of blade (42, 142) may provide such distal communication of the fluid. In some such versions, a particular vibrational scheme may be used to drive liquid distally along blade (42, 142). Such a particular, vibrational scheme may have no meaningful effect on tissue that is in contact with blade (42, 142) while blade is being driven in such a fashion. For instance, blade (42, 142) may be vibrated in short pulses (e.g., of approximately 10 to 20 millisecond duration) of low amplitude motion to drive the liquid distally along blade (42, 142). In some such instances, generator (16, 116) is programmed to provide such liquid driving ultrasonic activation of blade (42, 142) when the operator is not pressing any buttons (26, 126). In addition or in the alternative, generator (16, 116) may be programmed to provide liquid driving ultrasonic activation of blade (42, 142) when generator (16, 116) detects that blade (42, 142) is not contacting tissue. As yet another merely illustrative example, instrument (10, 100) may include a separate user input feature that is operable to manually trigger a liquid driving vibrational scheme. Other suitable ways in which a liquid driving vibrational scheme may be triggered will be apparent to those of ordinary skill in the art in view of the teachings herein.

In some other versions, the same vibrational movement that is used to drive blade during tissue cutting/sealing may drive liquid distally along blade (42, 142). As yet another merely illustrative example, fluid may be communicated to and/or along blade in accordance with at least some of the teachings of U.S. Pub. No. 2011/0152759, entitled "Use of Biomarkers and Therapeutic Agents with Surgical Devices," published Jun. 23, 2011, now U.S. Pat. No. 8,591,459, issued Nov. 26, 2013, the disclosure of which is incorporated by reference herein. It should be understood that the teachings in U.S. Pub. No. 2011/0152759, now U.S. Pat. No. 8,591,459, relating to dispensation of medical fluids may be readily adapted to provide communication of cooling fluid. Additional examples of ways in which fluid may be used to cool blade (42, 142) are described in U.S. Pub. No. 2015/0148832, entitled "Features to Apply Fluid to an Ultrasonic Blade of a Surgical Instrument," published May 28, 2015, issued as U.S. Pat. No. 10,034,685 on Jul. 31, 2018, the disclosure of which is incorporated by reference herein; U.S. Pub. No. 2015/0148835, entitled "Sleeve Features for Ultrasonic Blade of a Surgical Instrument," published May 28, 2015, issued as U.S. Pat. No. 10,004,528 on Jun. 26, 2018, the disclosure of which is incorporated by reference herein; U.S. Pub. No. 2016/0143658, entitled "Features to Drive Fluid toward an Ultrasonic Blade of a Surgical Instrument," published May 26, 2016, issued as U.S. Pat. No. 10,004,529 on Jun. 26, 2018, the disclosure of which is incorporated by reference herein; U.S. Pub. No. 2016/0143657, entitled "Features for Communication of Fluid through Shaft Assembly of Ultrasonic Surgical Instrument," published May 26, 2016, issued as U.S. Pat. No. 10,206,705 on Feb. 19, 2019, the disclosure of which is incorporated by reference herein; and U.S. Pub. No. 2016/0143659, entitled "Ultrasonic Surgical Instrument with Blade Cooling through Retraction," published May 26, 2016, issued as U.S. Pat. No. 10,433,863 on Oct. 8, 2019, the disclosure of which is incorporated by reference herein. It should be understood that the teachings herein may be readily combined with the teachings of those references and the various other references cited herein. Other examples will be apparent to those of ordinary skill in the art in view of the teachings herein.

In some instances, the heating at an end effector (40, 140) may be caused or hastened by direct contact between clamp pad (46, 146) and blade (42, 142) while clamp arm (44, 144) is closed and blade (42, 142) is activated, etc. Such direct contact may occur at regions where tissue is not interposed between clamp pad (46, 146) and blade (42, 142). Some operators may position tissue just between the distal portion of clamp pad (46, 146) and the distal portion of blade (42, 142). This may occur when end effector (40, 140) is used to transect relatively small vessels. When this occurs, the distal portions of clamp pad (46, 146) and blade (42, 142) may both contact the tissue compressed between clamp pad (46, 146) and blade (42, 142); yet the proximal portions of clamp pad (46, 146) and blade (42, 142) may just directly contact each other. When blade (42, 142) is activated in such instances, clamp pad (46, 146) and blade (42, 142) may rapidly generate a significant amount of heat at the proximal portions where the direct contact occurs.

It may therefore be desirable to minimize the amount of direct contact between clamp pad (46, 146) and blade (42, 142), particularly at the proximal regions of clamp pad (46, 146) and blade (42, 142). In other words, it may be desirable to provide staged engagement between clamp pad (46, 146) and blade (42, 142), such that the distal regions of clamp pad (46, 146) and blade (42, 142) engage first; then the proximal regions of clamp pad (46, 146) and blade (42, 142). Various examples of how an end effector (40, 140**) may provide such staged engagement are described in U.S. Provisional Patent App. No. 61/908,920, the disclosure of which is incorporated by reference herein; and also in U.S. Pub. No. 2015/0148834, entitled "Ultrasonic Surgical Instrument with Staged Clamping," published May 28, 2015, issued as U.S. Pat. No. 10,004,527 on Jun. 26, 2018, the disclosure of which is incorporated by reference herein. It should be understood that the teachings herein may be readily combined with the teachings of those references and the various other references cited herein. Other examples will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:

(a) a shaft assembly including an acoustic waveguide; and (b) an end effector distally extending from the shaft assembly, including:

(i) an ultrasonic blade distally extending from the acoustic waveguide and configured to treat tissue with an ultrasonic energy, wherein the ultrasonic blade has a first conductivity, (ii) a clamp arm configured to move relative to the ultrasonic blade from an open configuration for receiving a tissue toward a closed configuration for compressing a tissue against the ultrasonic blade, wherein the ultrasonic blade is configured to oscillate relative to the clamp arm, and (iii) an insulator positioned on the clamp arm and having a second conductivity different than the first conductivity of the ultrasonic blade, wherein the insulator has a distal-most tip and a proximal-most edge, wherein the insulator on the clamp arm covers an entirety of the clamp arm from the distal-most tip to the proximal-most edge, wherein the end effector is configured to conduct an electrical current to the tissue for sealing the tissue.

2. The surgical instrument of claim 1, wherein the insulator is positioned on the ultrasonic blade.

3. The surgical instrument of claim 1, wherein the insulator is positioned on the clamp arm.

4. The surgical instrument of claim 1, wherein the clamp arm includes a clamp pad, and wherein the insulator is positioned on the clamp pad.

5. The surgical instrument of claim 1, wherein the end effector further includes a shield positioned proximate to the ultrasonic blade.

6. The surgical instrument of claim 5, wherein the insulator is positioned on the shield.

7. The surgical instrument of claim 5, wherein the shield is selectively movable from a first position toward a second position in response to movement of the clamp arm toward the ultrasonic blade.

8. The surgical instrument of claim 7, wherein the shield is configured to cover at least a first portion of the ultrasonic blade in the first position, and wherein the shield is configured to uncover the first portion of the ultrasonic blade in the second position.

9. The surgical instrument of claim 5, wherein the shield is configured to cover at least a first portion of the end effector and define a gap therebetween.

10. The surgical instrument of claim 1, wherein the insulator includes a coating.

11. The surgical instrument of claim 1, wherein the second conductivity of the insulator is lower than the first conductivity of the ultrasonic blade.

12. The surgical instrument of claim 1, wherein the first conductivity includes a first thermal conductivity, and wherein the second conductivity includes a second thermal conductivity.

13. The surgical instrument of claim 12, wherein the second thermal conductivity of the insulator is lower than the first thermal conductivity of the ultrasonic blade.

14. The surgical instrument of claim 1, wherein the insulator includes a nanocomposite material.

15. The surgical instrument of claim 1, wherein the insulator defines a pair of ribs in contact with the clamp arm.

16. The surgical instrument of claim 15, wherein the pair of ribs extend longitudinally along an inner surface of the insulator.

17. A surgical instrument, comprising:

(a) a body configured to receive an ultrasonic transducer;

(b) a shaft assembly distally extending from the body and including an acoustic waveguide; and (c) an end effector distally extending from the shaft assembly, including:

(i) an ultrasonic blade distally extending from the acoustic waveguide and configured to treat tissue with an ultrasonic energy, wherein the ultrasonic blade has a first conductivity, (ii) a clamp arm configured to move relative to the ultrasonic blade from an open configuration for receiving a tissue toward a closed configuration for compressing a tissue against the ultrasonic blade, and (iii) an insulator positioned on the clamp arm and having a second conductivity lower than the first conductivity of the ultrasonic blade, wherein the insulator has a distal-most tip and a proximal-most edge, wherein the insulator on the clamp arm covers an entirety of the clamp arm from the distal-most tip to the proximal-most edge, wherein the end effector is configured to conduct an electrical current to the tissue for sealing the tissue.

18. The surgical instrument of claim 17, wherein the insulator includes a coating.

19. The surgical instrument of claim 18, wherein the clamp arm includes a clamp pad, and wherein the insulator is positioned on the clamp pad.

20. A surgical instrument, comprising:

(a) a shaft assembly including an acoustic waveguide; and (b) an end effector distally extending from the shaft assembly, including:

(i) an ultrasonic blade distally extending from the acoustic waveguide and configured to treat tissue with an ultrasonic energy, wherein the ultrasonic blade has a first thermal conductivity, wherein the ultrasonic blade is configured to mechanically modify tissue while vibrating at an ultrasonic frequency, (ii) a clamp arm configured to move relative to the ultrasonic blade from an open configuration for receiving a tissue toward a closed configuration for compressing a tissue against the ultrasonic blade, and (iii) a thermal insulator positioned on the clamp arm and having a second thermal conductivity different than the first thermal conductivity of the ultrasonic blade, wherein the thermal insulator has a distal-most tip and a proximal-most edge, wherein the thermal insulator on the clamp arm covers an entirety of the clamp arm from the distal-most tip to the proximal-most edge.

* * * * *